United States Patent
Slager et al.

(10) Patent No.: US 10,617,793 B2
(45) Date of Patent: *Apr. 14, 2020

(54) DELIVERY OF HYDROPHOBIC ACTIVE AGENT PARTICLES

(71) Applicant: Surmodics, Inc., Eden Prairie, MN (US)

(72) Inventors: Joram Slager, St. Louis Park, MN (US); Toni M. Heyer, St. Louis Park, MN (US); David E. Babcock, Brooklyn Park, MN (US)

(73) Assignee: Surmodics, Inc., Eden Prarie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/850,010

(22) Filed: Dec. 21, 2017

(65) Prior Publication Data

US 2018/0110903 A1    Apr. 26, 2018

Related U.S. Application Data

(63) Continuation of application No. 14/609,270, filed on Jan. 29, 2015, now Pat. No. 9,861,727, which is a continuation-in-part of application No. 13/793,390, filed on Mar. 11, 2013, which is a continuation-in-part of application No. 13/469,844, filed on May 11, 2012, now Pat. No. 9,757,497.

(60) Provisional application No. 61/488,582, filed on May 20, 2011.

(51) Int. Cl.
| | |
|---|---|
| *A61L 29/08* | (2006.01) |
| *A61L 29/16* | (2006.01) |
| *A61L 29/14* | (2006.01) |
| *A61K 31/337* | (2006.01) |
| *A61K 31/713* | (2006.01) |
| *A61K 47/34* | (2017.01) |
| *A61M 25/10* | (2013.01) |
| *C12N 15/113* | (2010.01) |
| *A61K 9/50* | (2006.01) |

(52) U.S. Cl.
CPC .......... *A61L 29/085* (2013.01); *A61K 31/337* (2013.01); *A61K 31/713* (2013.01); *A61K 47/34* (2013.01); *A61L 29/14* (2013.01); *A61L 29/16* (2013.01); *A61M 25/10* (2013.01); *C12N 15/113* (2013.01); *A61K 9/5031* (2013.01); *A61L 2300/258* (2013.01); *A61L 2300/416* (2013.01); *A61L 2300/606* (2013.01); *A61L 2300/608* (2013.01); *A61L 2300/62* (2013.01); *A61L 2300/802* (2013.01); *A61L 2420/06* (2013.01); *A61L 2420/08* (2013.01); *A61M 2025/105* (2013.01); *C12N 2310/14* (2013.01); *C12N 2320/32* (2013.01)

(58) Field of Classification Search
CPC combination set(s) only.
See application file for complete search history.

(56) References Cited

U.S. PATENT DOCUMENTS

| | | |
|---|---|---|
| 3,389,099 A | 6/1968 | Dressler et al. |
| 3,936,391 A | 2/1976 | Gabby et al. |
| 4,195,637 A | 4/1980 | Gruntzig et al. |
| 4,456,627 A | 6/1984 | Van Heteren et al. |
| 4,490,421 A | 12/1984 | Levy |
| 4,638,045 A | 1/1987 | Kohn et al. |
| 4,722,906 A | 2/1988 | Guire |
| 4,973,493 A | 11/1990 | Guire |
| 4,979,959 A | 12/1990 | Guire |
| 5,002,582 A | 3/1991 | Guire et al. |
| 5,041,089 A | 8/1991 | Mueller et al. |
| 5,073,641 A | 12/1991 | Bundgaard et al. |
| 5,087,246 A | 2/1992 | Smith |
| 5,102,402 A | 4/1992 | Dror et al. |
| 5,201,753 A | 4/1993 | Lampropoulos et al. |
| 5,263,992 A | 11/1993 | Guire |
| 5,297,607 A | 3/1994 | Beauchamp |
| 5,304,121 A | 4/1994 | Sahatjian |
| 5,318,587 A | 6/1994 | Davey |
| 5,334,146 A | 8/1994 | Ozasa |
| 5,382,234 A | 1/1995 | Cornelius et al. |

(Continued)

FOREIGN PATENT DOCUMENTS

| | | |
|---|---|---|
| CA | 2836266 | 11/2012 |
| CA | 2760187 | 1/2018 |

(Continued)

OTHER PUBLICATIONS

Akiyama, Yohko et al., "In Vitro and in Vivo evaluation of Mucoadhesive Microspheres Prepared for the Gastrointestinal Tract Using Polyglycerol Esters of Fatty Acids and a Poly(acrylic acid) Derivative," Pharmaceutical Research, vol. 12, No. 3, 1995, 397-405.

(Continued)

*Primary Examiner* — Robert S Cabral
(74) *Attorney, Agent, or Firm* — Pauly, DeVries Smith & Deffner LLC

(57) ABSTRACT

Embodiments of the invention include drug delivery coatings and devices including the same. In an embodiment, the invention includes a drug delivery coating including a polymeric layer. The polymeric layer can include a hydrophilic outer surface. The coating can also include a matrix contacting the hydrophilic outer surface. The matrix can include a particulate hydrophobic therapeutic agent and a cationic agent. The polymeric layer can further include a hydrophilic polymer having pendent photoreactive groups and a photo-crosslinker including two aryl ketone functionalities. Other embodiments are also included herein.

20 Claims, 6 Drawing Sheets

(56) References Cited

U.S. PATENT DOCUMENTS

| | | |
|---|---|---|
| 5,397,307 A | 3/1995 | Goodin |
| 5,414,075 A | 5/1995 | Swan et al. |
| 5,466,719 A | 11/1995 | Jakobson et al. |
| 5,502,219 A | 3/1996 | Harris |
| 5,512,329 A | 4/1996 | Guire et al. |
| 5,556,383 A | 9/1996 | Wang et al. |
| 5,558,642 A | 9/1996 | Schweich, Jr. et al. |
| 5,571,089 A | 11/1996 | Crocker |
| 5,585,506 A | 12/1996 | Harvey |
| 5,616,608 A | 4/1997 | Kinsella et al. |
| 5,632,773 A | 5/1997 | Graham et al. |
| 5,637,460 A | 6/1997 | Swan et al. |
| 5,714,360 A | 2/1998 | Swan et al. |
| 5,728,732 A | 3/1998 | Corey |
| 5,741,551 A | 4/1998 | Guire et al. |
| 5,776,101 A | 7/1998 | Goy |
| 5,807,331 A | 9/1998 | Den Heijer et al. |
| 5,811,447 A | 9/1998 | Kunz et al. |
| 5,833,657 A | 11/1998 | Reinhardt et al. |
| 5,858,653 A | 1/1999 | Duran et al. |
| 5,882,336 A | 3/1999 | Janacek |
| 5,891,451 A | 4/1999 | Guerrero et al. |
| 5,980,948 A | 11/1999 | Goedemoed et al. |
| 6,007,833 A | 12/1999 | Chudzik et al. |
| 6,077,698 A | 6/2000 | Swan et al. |
| 6,168,748 B1 | 1/2001 | Wang et al. |
| 6,177,522 B1 | 1/2001 | Brady et al. |
| 6,210,364 B1 | 4/2001 | Anderson et al. |
| 6,278,018 B1 | 8/2001 | Swan |
| 6,299,604 B1 | 10/2001 | Ragheb et al. |
| 6,328,710 B1 | 12/2001 | Wang et al. |
| 6,340,465 B1 | 1/2002 | Hsu et al. |
| 6,394,995 B1 | 5/2002 | Solar et al. |
| 6,436,440 B1 | 8/2002 | Meffert et al. |
| 6,444,324 B1 | 9/2002 | Sjoquist et al. |
| 6,465,178 B2 | 10/2002 | Chappa et al. |
| 6,482,348 B1 | 11/2002 | Wang et al. |
| 6,506,411 B2 | 1/2003 | Hunter et al. |
| 6,506,895 B2 | 1/2003 | Guire et al. |
| 6,514,734 B1 | 2/2003 | Clapper et al. |
| 6,515,009 B1 | 2/2003 | Kunz et al. |
| 6,517,515 B1 | 2/2003 | Eidenschink |
| 6,544,544 B2 | 4/2003 | Hunter et al. |
| 6,603,040 B1 | 8/2003 | Swan |
| 6,613,066 B1 | 9/2003 | Fukaya et al. |
| 6,620,904 B2 | 9/2003 | Lemke |
| 6,623,452 B2 | 9/2003 | Chien et al. |
| 6,623,504 B2 | 9/2003 | Vrba et al. |
| 6,663,662 B2 | 12/2003 | Pacetti et al. |
| 6,703,040 B2 | 3/2004 | Katsarava et al. |
| 6,730,064 B2 | 5/2004 | Ragheb et al. |
| 6,762,019 B2 | 7/2004 | Swan et al. |
| 6,896,842 B1 | 5/2005 | Hamilton et al. |
| 7,138,541 B2 | 11/2006 | Swan |
| 7,163,523 B2 | 1/2007 | Devens, Jr. et al. |
| 7,309,593 B2 | 12/2007 | Ofstead et al. |
| 7,348,055 B2 | 3/2008 | Chappa et al. |
| 7,438,710 B2 | 10/2008 | Anderson et al. |
| 7,507,469 B2 | 3/2009 | Yao et al. |
| 7,696,259 B2 | 4/2010 | Hanley et al. |
| 7,731,685 B2 | 6/2010 | Schaeffer et al. |
| 7,736,689 B2 | 6/2010 | Chappa et al. |
| 7,758,892 B1 | 7/2010 | Chen et al. |
| 7,772,393 B2 | 8/2010 | Guire et al. |
| 7,797,033 B2 | 9/2010 | D'andrea et al. |
| 7,803,149 B2 | 9/2010 | Schaeffer et al. |
| 7,807,750 B2 | 10/2010 | Taton et al. |
| 7,820,193 B2 | 10/2010 | Hunter et al. |
| 7,850,727 B2 | 12/2010 | Shanley et al. |
| 8,034,765 B2 | 10/2011 | De et al. |
| 8,039,524 B2 | 10/2011 | Ralph et al. |
| 8,158,106 B2 | 4/2012 | Guire et al. |
| 8,172,793 B2 | 5/2012 | Choules et al. |
| 8,202,530 B2 | 6/2012 | Hossainy et al. |
| 8,246,576 B2 | 8/2012 | Slager |
| 8,257,305 B2 | 9/2012 | Scheller et al. |
| 8,293,262 B2 | 10/2012 | Chen et al. |
| 8,439,868 B2 | 5/2013 | Scheller et al. |
| 8,469,943 B2 | 6/2013 | Bates et al. |
| 8,487,137 B2 | 7/2013 | Guire et al. |
| 8,513,320 B2 | 8/2013 | Rooijmans |
| 8,557,272 B2 | 10/2013 | Zhao et al. |
| 8,673,387 B2 | 3/2014 | Bates et al. |
| 8,697,112 B2 | 4/2014 | Ditizio et al. |
| 8,809,411 B2 | 8/2014 | Rooijmans |
| 8,871,819 B2 | 10/2014 | Meyering et al. |
| 8,889,760 B2 | 11/2014 | Kurdyumov et al. |
| 8,952,103 B2 | 2/2015 | Blondel et al. |
| 9,375,517 B2 | 6/2016 | Babcock |
| 9,555,119 B2 | 1/2017 | Ventura et al. |
| 9,757,497 B2 | 9/2017 | Slager |
| 9,861,727 B2 | 1/2018 | Slager et al. |
| 9,999,675 B2 | 6/2018 | Ventura et al. |
| 10,058,634 B2 | 8/2018 | Chappa et al. |
| 2002/0006493 A1 | 1/2002 | Chabrecek et al. |
| 2002/0123801 A1 | 9/2002 | Pacetti et al. |
| 2003/0065355 A1 | 4/2003 | Weber |
| 2003/0195611 A1 | 10/2003 | Greenhalgh et al. |
| 2003/0211135 A1 | 11/2003 | Greenhalgh et al. |
| 2004/0044404 A1 | 3/2004 | Stucke et al. |
| 2004/0051201 A1 | 3/2004 | Greenhalgh et al. |
| 2004/0105839 A1 | 6/2004 | Park |
| 2004/0117007 A1 | 6/2004 | Whitbourne et al. |
| 2005/0100580 A1 | 5/2005 | Osborne et al. |
| 2005/0187605 A1 | 8/2005 | Greenhalgh et al. |
| 2005/0255142 A1 | 11/2005 | Chudzik et al. |
| 2005/0281857 A1 | 12/2005 | Heyer et al. |
| 2006/0018948 A1 | 1/2006 | Guire et al. |
| 2006/0020243 A1 | 1/2006 | Speck et al. |
| 2006/0030669 A1 | 2/2006 | Taton et al. |
| 2006/0148982 A1 | 7/2006 | Uchegbu et al. |
| 2006/0200232 A1 | 9/2006 | Phaneuf et al. |
| 2006/0240194 A1 | 10/2006 | Lemke et al. |
| 2007/0026037 A1 | 2/2007 | Kloke et al. |
| 2007/0032882 A1 | 2/2007 | Lodhi et al. |
| 2007/0048351 A1 | 3/2007 | Lunn |
| 2007/0065481 A1 | 3/2007 | Chudzik et al. |
| 2007/0154591 A1 | 7/2007 | Andersen |
| 2007/0155906 A1 | 7/2007 | Hissink et al. |
| 2007/0218102 A1 | 9/2007 | Chudzik et al. |
| 2007/0224247 A1 | 9/2007 | Chudzik et al. |
| 2007/0260054 A1 | 11/2007 | Chudzik |
| 2008/0020013 A1 | 1/2008 | Reyes et al. |
| 2008/0220054 A1 | 9/2008 | Shastri et al. |
| 2008/0233183 A1 | 9/2008 | Mccook et al. |
| 2009/0030504 A1 | 1/2009 | Weber et al. |
| 2009/0043276 A1 | 2/2009 | Weber et al. |
| 2009/0043378 A1 | 2/2009 | Cheng et al. |
| 2009/0081276 A1 | 3/2009 | Alsberg et al. |
| 2009/0221767 A1 | 9/2009 | Malet |
| 2009/0226501 A1 | 9/2009 | Parsonage et al. |
| 2009/0227946 A1 | 9/2009 | Kangas |
| 2010/0015240 A1 | 1/2010 | Biggs |
| 2010/0040766 A1 | 2/2010 | Chappa et al. |
| 2010/0076377 A1 | 3/2010 | Ehrenreich et al. |
| 2010/0076401 A1 | 3/2010 | Von et al. |
| 2010/0087783 A1 | 4/2010 | Weber et al. |
| 2010/0096320 A1 | 4/2010 | Opperman et al. |
| 2010/0130837 A1 | 5/2010 | Matott |
| 2010/0198168 A1 | 8/2010 | Rooijmans |
| 2010/0272774 A1 | 10/2010 | Chappa |
| 2010/0274012 A1 | 10/2010 | Guire et al. |
| 2010/0292668 A1 | 11/2010 | Slager |
| 2011/0022027 A1 | 1/2011 | Morishita et al. |
| 2011/0046255 A1 | 2/2011 | Rooijmans |
| 2011/0059874 A1 | 3/2011 | Rooijmans et al. |
| 2011/0144373 A1 | 6/2011 | Swan et al. |
| 2011/0245367 A1 | 10/2011 | Kurdyumov et al. |
| 2011/0250255 A1 | 10/2011 | Parsonage et al. |
| 2011/0257339 A1 | 10/2011 | Fischer et al. |
| 2011/0275725 A1 | 11/2011 | Meyering et al. |
| 2012/0039983 A1 | 2/2012 | Uhrich et al. |
| 2012/0046384 A2 | 2/2012 | Kurdyumov et al. |
| 2012/0083734 A1 | 4/2012 | Ayres et al. |

(56) References Cited

U.S. PATENT DOCUMENTS

| | | |
|---|---|---|
| 2012/0148852 A1 | 6/2012 | Jelle et al. |
| 2012/0149934 A1 | 6/2012 | Kurdyumov |
| 2012/0177742 A1 | 7/2012 | Mcclain et al. |
| 2012/0177910 A1 | 7/2012 | Weber et al. |
| 2012/0296274 A1 | 11/2012 | Slager |
| 2013/0143056 A1 | 6/2013 | Swan et al. |
| 2013/0190689 A1 | 7/2013 | Slager |
| 2013/0197433 A1 | 8/2013 | Babcock |
| 2013/0302529 A1 | 11/2013 | Kurdyumov |
| 2014/0004158 A1 | 1/2014 | Mcgonigle |
| 2014/0142166 A1 | 5/2014 | Ventura |
| 2014/0162083 A1 | 6/2014 | Kurdyumov et al. |
| 2014/0193474 A1 | 7/2014 | Babcock et al. |
| 2014/0276636 A1 | 9/2014 | Lee et al. |
| 2014/0336571 A1 | 11/2014 | Slager |
| 2015/0140107 A1 | 5/2015 | Slager et al. |
| 2015/0283092 A1 | 10/2015 | Ruddy et al. |
| 2017/0072057 A1 | 3/2017 | Ventura et al. |
| 2017/0112973 A1 | 4/2017 | Slager et al. |
| 2018/0169032 A1 | 6/2018 | Kloke |
| 2018/0272040 A1 | 9/2018 | Chappa et al. |

FOREIGN PATENT DOCUMENTS

| | | |
|---|---|---|
| CN | 1413118 | 4/2003 |
| CN | 1950114 | 4/2007 |
| CN | 1964750 | 5/2007 |
| CN | 104185661 | 8/2016 |
| CN | 103906505 | 1/2018 |
| CR | 2014-0349 | 11/2014 |
| EP | 0882461 | 12/1998 |
| EP | 1176993 | 6/2003 |
| EP | 1994950 | 11/2008 |
| EP | 1997525 | 12/2008 |
| EP | 2251050 | 11/2010 |
| EP | 2098230 | 6/2012 |
| EP | 2292225 | 6/2012 |
| EP | 2569023 | 10/2015 |
| EP | 2804915 | 3/2016 |
| EP | 3012301 | 4/2016 |
| EP | 2424581 | 3/2017 |
| IN | 6113/CHENP/2014 A | 7/2016 |
| JP | 2009502243 | 1/2009 |
| JP | 2014515348 | 6/2014 |
| JP | 5814913 | 10/2015 |
| JP | 6140690 | 5/2017 |
| WO | 9964086 | 12/1999 |
| WO | 0110468 | 2/2001 |
| WO | 2001045742 | 6/2001 |
| WO | 03055611 | 7/2003 |
| WO | 2004017943 | 5/2004 |
| WO | 2005079754 | 9/2005 |
| WO | 2005113034 | 12/2005 |
| WO | 2006019848 | 2/2006 |
| WO | 2006026187 | 3/2006 |
| WO | 2006053175 | 5/2006 |
| WO | 2007012051 | 1/2007 |
| WO | 2007106441 | 9/2007 |
| WO | 2007136504 | 11/2007 |
| WO | 2009051614 | 4/2009 |
| WO | 2009113605 | 9/2009 |
| WO | 2009121629 | 10/2009 |
| WO | 2011024831 | 8/2010 |
| WO | 2010111517 | 9/2010 |
| WO | 2010129328 | 11/2010 |
| WO | 2011005421 | 1/2011 |
| WO | 2011052089 | 5/2011 |
| WO | 2012003293 | 1/2012 |
| WO | 2012162061 | 11/2012 |
| WO | 2013109930 | 7/2013 |
| WO | 2013169879 | 11/2013 |
| WO | 2014071387 | 5/2014 |
| WO | 2014186729 | 11/2014 |
| WO | 2016123480 | 8/2016 |
| WO | 2018118671 | 6/2018 |

OTHER PUBLICATIONS

Avella, "Addition of glycerol plasticizer to seaweeds derived alginates: Influences of microstructure on chemical-physical properties," Carbohydrate Polymers vol. 69, Issue 3, Jun. 25, 2007, 503-511.

Babayan, V K. "Preparation and Properties of Some Polyglycerol Esters of Short and Medium Length Fatty Acids," Journal of the American Oil Chemists' Society Jul. 1971, 307-309.

Babayan, V K. et al., "Nutritional Studies of Polyglycerol Esters," The Journal of the American Oil Chemist' Society vol. 41, Jun. 1964, 434-438.

Birnbaum, Duane T. et al., "Microparticle Drug Delivery Systems," Chapter 6, Drug Delivery Systems in Cancer Therapy, 2003, (pp. 117-135).

Bodansky, M et al., "Utilization of Polyglycerol Esters," Biochemistry vol. 32 Aug. 30, 1938, 1938-1942.

Charlemagne, D et al., "Enzymatic Synthesis of Polyglycerol-Fatty Acid Esters in a Solvent-Free System," Journal for American Oil Chemists' Society vol. 72. No. 1 (1995), 61-65.

"Communication Pursuant to Article 94(3) EPC," for European Application No. 10716714, dated Feb. 13, 2015 (6 pages).

"Communication Pursuant to Article 94(3) EPC," for European Application No. 10716714, dated Jan. 18, 2013 (5 pages).

"Communication Pursuant to Article 94(3) EPC," for European Application No. 13792207.6, dated Sep. 29, 2017 (5 pages).

"Communication Pursuant to Article 94(3) EPC," for European Patent Application No. 12723063.9 dated Jun. 12, 2017 (5 pages).

"Communication Pursuant to Article 94(3) EPC," for European Patent Application No. 14730381.2 dated Nov. 21, 2017 (4 pages).

"Communication Pursuant to Rules 161(1) and 162 EPC," for European Application No. 13792207.6, dated Aug. 5, 2015 (2 pages).

"Communication Pursuant to Rules 161(1) and 162 EPC," for European Patent Application No. 12723063.9, dated Jan. 21, 2014 (2 pages).

"Communication Pursuant to Rules 161(1) and 162 EPC," for European Patent Application No. 14730381.2, dated Jan. 15, 2016 (2 pages).

"Communication Pursuant to Rules 161(1) and 162 EPC," for European Patent Application No. 16703247.3 dated Sep. 15, 2017 (2 pages).

De Meulenaer, B et al., "Development of Chromatographic Method for the Determination of Degree of Polymerisation of Polyglycerols and Polyglycerol Fatty Acid Esters," Chromatographia vol. 51, No. 1/2, Jan. 2000, 44-52.

"Decision of Refusal," for Japanese Patent Application No. 2012-508637, dated Feb. 3, 2015 (3 pages) with English summary.

Dobson, Kevin S. et al., "The Preparation of Polyglycerol Esters Suitable as Low-Caloric Fat Substitutes," Journal of the American Oil Chemists' Society vol. 70, No. 11 (Nov. 1993), 1089-1092.

Dow Corning Corp., "A guide to Silane Solutions," 2005 (30 pages).

FAO Nutrition Meetings Report, "Toxicological Evaluation of Some Antimicrobials, Antioxidants, Emulsifiers, Stabilizers, Flour-treatment Agents, Acids and Bases," FAO Nutrition Meetings Report Series No. 40A, B, C WHO/ Food Add. 67.29 1966, 1-4.

"File History," for U.S. Appl. No. 12/769,127.
"File History," for U.S. Appl. No. 13/469,844.
"File History," for U.S. Appl. No. 13/793,390.
"File History," for U.S. Appl. No. 14/072,520.
"File History," for U.S. Appl. No. 14/280,170.
"File History," for U.S. Appl. No. 14/609,270.
"File History," for U.S. Appl. No. 15/357,496.
"File History," for U.S. Appl. No. 15/385,112.

Finkel, Toren "Relief with Rapamycin: mTOR Inhibition Protects Against Radiation-Induced Mucositis," Cell Stem Cell, vol. 11:3, Sep. 7, 2012 (pp. 1-4).

"First Office Action," for Chinese Application No. 201080018767.7 dated Jun. 8, 2013 (9 pages).

"First Office Action," for Chinese Patent Application No. 2012800328049, dated Mar. 2, 2015 (12 pages) including English translation.

(56) References Cited

OTHER PUBLICATIONS

"First Office Action," for Chinese Patent Application No. 201510411761.0 dated Jun. 30, 2017 (13 pages) with English translation.
"Fourth Office Action," for Chinese Patent Application No. 2012800328049, dated May 3, 2017 (8 pages) with English translation.
From Wikipedia, "Electrospinning," From Wikipedia, the free encyclopedia, http://en.wikipedia.org/wiki/Electrospinning, downloaded Sep. 13, 2010; last updated Sep. 2, 2010, 2009, (pp. 1-6).
Ghonaim, Hassan M. et al., "N1,N12-Diacyl Spermines: SAR Studies on Non-viral Lipopolyamine Vectors for Plasmid DNA and siRNA Formulation," Pharmaceutical Research, vol. 27, No. 1, Jan. 2010 (p. 17-29).
Hagemeier, C J. "Ocular Tolerability of Poly(lactide-co-glyoliide) Microspheres Following Subconjunctival and Inravitreal Injection in Rabbit Eyes," ARVO 2010 Presented ARVO 2010, Hall B/C, May 6, 2010 8:30am-10:15am May 6, 2010.
Howes, D et al., "The Fate of Ingested Glyceran Esters of Condensed Castor Oil Fatty Acids [Polyglycerol Polyricinoleate (PGPR)] in the Rat," Food and Chemical Toxicology 36 (1998) 719-738 1998.
"International Preliminary Report on Patentability," for PCT Application No. PCT/US2016/015644 dated Aug. 10, 2017 (12 pages).
"International Preliminary Report on Patentability," for PCT/US2012/038158, dated Nov. 28, 2013 (8 pages).
"International Preliminary Report on Patentability," for PCT/US2013/068539, dated May 14, 2015 (9 pages).
"International Preliminary Report on Patentability," for PCT/US2014/038435 dated Nov. 26, 2015 (10 pages).
"International Search Report & Written Opinion," for PCT/US2016/015644 dated Jul. 11, 2016 (17 pages).
"International Search Report and Written Opinion," for PCT/US2010/032741 dated Dec. 13, 2010 (11 pages) dated Dec. 13, 2010, 11 pages.
"International Search Report and Written Opinion," for PCT/US2012/038158, dated Sep. 27, 2012 (13 pages).
"International Search Report and Written Opinion," for PCT/US2013/068539, dated Jan. 22, 2014 (12 pages).
"International Search Report and Written Opinion," for PCT/US2014/038435, dated Aug. 25, 2014 (13 pages).
"International Search Report and Written Opinion," for PCT Application No. PCT/US2017/066573 dated Apr. 3, 2018 (10 pages).
"Invitation to Pay Additional Fees and Partial Search Report," for PCT Application No. PCT/US2016/015644, dated May 3, 2016 (8 pages).
"Invitation to Respond to Written Opinion," for SG Patent Application No. 201107896-1, dated Jun. 12, 2012 (6 pages).
Kallinteri, Paraskevi et al., "Novel Functionalized Biodegradable Polymers for Nanoparticle Drug Delivery Systems," Biomacromolecules 2005 2006, 6, 1885-1894; American Chemical Society Apr. 27, 2005.
Kumar, Majeti N.V. R. "Nano and Microparticles as Controlled Drug Delivery Devices," J. Pharm Pharmaceut Sci, 3(2), 2000 (pp. 234-258).
Liu, Rong "Water-Insoluble Drug Formulation," CRC Press, 2nd Ed., 2008 (pp. 1-3).
Love, Kevin T. et al., "Lipid-Like Materials for Low-Dose In Vivo Gene Silencing," PNAS Feb. 2010, 107 (5) 1864-1869, www.pnas.org/cgi/doi/10.1073/pnas.0910603106 (6 pages).
McIntyre, R T. "Polyglycerol esters," Journal of American Oil Chemists' Society Nov. 1979 (vol. 56) Nov. 1979, 835A-840A.
Mugabe, Clement et al., "Paclitaxel Incorporated in Hydrophobically Derivated Hyperbranched Polyglycerols for Intravesical Bladder Cancer Therapy," BJU International, 2008, vol. 103, p. 978-986.
"Non-Final Office Action," for Japanese Patent Application No. 2012-508637, dated Mar. 18, 2014 (4 pages) with English translation.
"Non-Final Office Action," for Mexican Patent Application No. MX/a/2011/011389, dated Aug. 18, 2015 (1 page).

"Non-Final Office Action," for Mexican Patent Application No. MX/a/2011/011389, dated Feb. 22, 2016 (1 page).
"Notification for Patent Reexamination," for Chinese Patent Application No. 201080018767.7, dated Sep. 25, 2014 (12 pages) with English translation.
"Office Action," for Canadian Patent Application No. 2,760,187 dated Jan. 12, 2017 (3 pages).
"Office Action," for Canadian Patent Application No. 2,760,187 dated Mar. 24, 2016 (4 pages).
"Office Action," for Canadian Patent Application No. 2,836,266 dated Apr. 11, 2018 (3 pages).
"Office Action," for Japanese Patent Application No. 2014511494 dated Feb. 5, 2016 (13 pages) with English Translation.
"Office Action," for Japanese Patent Application No. 2014511494 dated Nov. 25, 2016 (6 pages) with English Translation.
"Office Action," for Japanese Patent Application No. 2015-540868 dated Aug. 31, 2017 (10 pages) with English translation.
"Office Action," for Japanese Patent Application No. 2015-540868 dated May 21, 2018 (6 pages) with English translation.
"Office Action," for Japanese Patent Application No. 2016-514136 dated Apr. 10, 2018 (7 pages) with English translation.
Orafei, Hossein et al., "Novel Poly(glycerol-adipate) Polymers Used for Nanoparticle Making: A Study of Surface Free Energy," Iranian Journal of Pharmaceutical Research (2008), 7 (1): Nov. 19, 2008, 11-19.
"PCT Notification Concerning Transmittal of International Preliminary Report on Patentability," from International Application No. PCT/US10/032741, dated Nov. 10, 2011, pp. 1-8.
Puri, Sanyogita "Drug Incorporation and Release of Water Soluble Drugs from Novel Functionalized Poly(glycerol adipate) Nanoparticles," Journal of Controlled Release 125 (2008) 59-67.
Renkin, Eugene M. "Filtration, Diffusion, and Molecular Sieving Through Porous Cellulose Membranes," Nov. 20, 1954 (pp. 1-19).
"Response to Communication Pursuant to Article 94(3) EPC," for European Application No. 10716714.0 filed with EPO dated Aug. 11, 2015 (51 pages).
"Response to Communication Pursuant to Article 94(3) EPC," for European Application No. 10716714.0 filed with EPO dated Jun. 10, 2013 (9 pages).
"Response to Communication Pursuant to Article 94(3) EPC," for European Patent Application No. 12723063.9 filed with the EPO dated Nov. 16, 2017 (9 pages).
"Response to Communication Pursuant to Article 94(3) EPC," for European Patent Application No. 13792207.6, filed with the EPO dated Mar. 29, 2018 (25 pages).
"Response to Communication Pursuant to Article 94(3) EPC," for European Patent Application No. 14730381.2, filed with the European Patent Office dated Dec. 21, 2017 (68 pages).
"Response to Communication Pursuant to Rule 161 and 162 EPC," for European Patent Application 12723063.9, dated Jan. 21, 2014 and filed with the EPO dated Jul. 18, 2014 (4 pages).
"Response to Communication Pursuant to Rules 161(1) and 162 EPC," for European Application No. 13792207.6, filed with the EPO dated Feb. 3, 2016 (4 pages).
"Response to Communication Pursuant to Rules 161(1) and 162 EPC," for European Patent Application No. 14730381.2, filed with the European Patent Office dated Jul. 14, 2016 (14 pages).
"Response to Communication Pursuant to Rules 161(1) and 162 EPC," for European Patent No. 16703247.3 filed with the EPO dated Mar. 22, 2018.
"Response to Office Action," for Canadian Patent Application No. 2,760,187 filed with CIPO dated Feb. 15, 2017 (5 pages).
"Response to Office Action," for Canadian Patent Application No. 2,760,187 filed with CIPO dated Sep. 22, 2016 (22 pages).
Salamone, Joseph "Hydrophic Polymers (for Friction Reduction)," Polymeric Materials Encyclopedia, vol. 12 (1996) p. 3107.
Santoyo, Antonio B. et al., "Biosynthesis of Polyglycerol Polyricinoleate (PGPR) with Rhizopus Arrhizus Lipase," Journal of Biotechnology 131S (2007) S74-S97 2007, S82.
Scheller, Bruno et al., "Paclitaxel Balloon Coating, a Novel Method for Prevention and Therapy of Restenosis," Circulation, Journal of the American Heart Association; 2004 (110);810-814. Online ver-

(56) References Cited

OTHER PUBLICATIONS sion of article: http://circ.ahajournals.org/cgi/content/full/11/7/810, downloaded Jan. 12, 2011 2004, 6 pages.
"Second Office Action," for China Patent Application No. 2012800328049, dated Jan. 26, 2016 (9 pages), with translation.
"Second Office Action," for Chinese Patent Application No. 201510411761.0 dated Dec. 22, 2017 (11 pages) with English translation.
Solvay Chemicals, "Polyglycerols for Ester Production," PGLC-05-002 Revised Aug. 2008 CGR4004, From www.solvaychemicals.us Aug. 2008, 1-7.
Takatori, Toshihito "Design of Controlled-Release Morphine Suppositories Containing Polyglycerol Ester of Fatty Acid," Biological Phamacy Bulletin 28(8) 1480-1484 (2005), vol. 28, No. 8.
"Third Office Action," for Chinese Patent Application No. 2012800328049, dated Aug. 11, 2016 (12 pages) with English translation.
Yamagata, Yutaka et al., "Novel Sustained Release Dosage Forms of Proteins Using Polyglycerol Esters of Fatty Acids," Journal of Controlled Release vol. 63, Issue 3 Feb. 3, 2000, 319-329.
"Non-Final Office Action," for U.S. Appl. No. 13/793,390 dated Jul. 13, 2018 (48 pages).
"Non-Final Office Action," for U.S. Appl. No. 15/385,112 dated Aug. 13, 2018 (8 pages).
"Response to Non-Final Rejected," dated Aug. 13, 2018, for U.S. Appl. No. 15/385,112, submitted via EFS-Web on Sep. 12, 2018, 5 pages.
"Response to Non-Final Rejection," dated Jul. 13, 2018, for U.S. Appl. No. 13/793,390, submitted via EFS-Web on Sep. 12, 2018, 6 pages.
"Third Office Action," for Chinese Patent Application No. 201510411761.0 dated Jul. 25, 2018 (14 pages) with English translation.
"Communication Pursuant to Article 94(3) EPC," for European Patent Application No. 16703247.3 dated Sep. 4, 2018 (5 pages).
"Decision of Rejection," for Chinese Patent Application No. 201510411761.0 dated Nov. 30, 2018 (19 pages) with English Translation.
"First Examination Report," for Indian Patent Application No. 3723/KOLNP/2013 dated Sep. 28, 2018 (5 pages).
"Non Final Office Action," for U.S. Appl. No. 14/280,170 dated Oct. 5, 2018 (36 pages).
"Non-Final Office Action," for U.S. Appl. No. 15/840,540 dated Oct. 17, 2018 (38 pages).
"Notice of Allowance," for U.S. Appl. No. 13/793,390 dated Oct. 31, 2018 (10 pages).
"Notice of Allowance," for U.S. Appl. No. 15/385,112 dated Oct. 5, 2018 (10 pages).
"Office Action," for Canadian Patent Application No. 2,836,266 dated Nov. 30, 2018 (4 pages).
"Office Action," for Mexican Patent Application No. MX/a/2015/015589 dated Sep. 9, 2018 (1 page), translation only.
"Product Data Sheet," for PEBAX MV 1074 SA 01 MED from Arkema (2013, pp. 1-2) 2 pages.
"Response to Communication Pursuant to Article 94(3) EPC," for European Patent Application No. 16703247.3 filed Dec. 20, 2018 (7 pages).
"Response to Non Final Office Action," for U.S. Appl. No. 14/280,170, filed Dec. 10, 2018 (18 pages).
"Response to Non-Final Office Action," for U.S. Appl. No. 15/840,540, filed Dec. 20, 2018 (9 pages).
"Response to Office Action," for Canadian Patent Application No. 2,836,266 filed with CIPO dated Sep. 20, 2018 (28 pages).
"Communication Pursuant to Article 94(3) EPC," for European Patent Application No. 12723063.9 dated Jan. 16, 2019 (5 pages).
"Communication Pursuant to Article 94(3) EPC," for European Patent Application No. 16703247.3 dated Apr. 23, 2019 (5 pages).
"Final Office Action," for U.S. Appl. No. 14/280,170 dated Apr. 5, 2019 (38 pages).
"Non-Final Office Action," for U.S. Appl. No. 15/840,540 dated Mar. 15, 2019 (15 pages).
"Office Action," for Israeli Patent Application No. 242545 dated May 28, 2019 (8 pages) with English Translation.
"Response to Final Rejection," dated Mar. 15, 2019 for U.S. Appl. No. 15/840,540, submitted via EFS-Web on May 15, 2019, 13 pages.
"Response to First Examination Report," for Indian Patent Application No. 3723/KOLNP/2013 filed Feb. 20, 2019 (23 pages).
"Response to Office Action," for Canadian Patent Application No. 2,836,266 filed May 29, 2019 (19 pages).
"First Office Action," for Russian Patent Application No. 2017129933 dated Jun. 27, 2019 (10 pages) with English Translation.
"International Preliminary Report on Patentability," for PCT Application No. PCT/US2017/066573 dated Jul. 4, 2019 (7 pages).
"Non-Final Office Action," for U.S. Appl. No. 15/840,540 dated Aug. 20, 2019 (20 pages).
"Non-Final Office Action," for U.S. Appl. No. 15/994,263 dated Aug. 14, 2019 (50 pages).
"Response to Communication Pursuant to Article 94(3) EPC," for European Patent Application No. 12723063.9 filed Jul. 2, 2019 (56 pages).
"Response to Communication Pursuant to Article 94(3) EPC," for European Patent Application No. 16703247.3 filed Aug. 30, 2019 (10 pages).
"Response to Final Rejection," dated Apr. 5, 2019 for U.S. Appl. No. 14/280,170, submitted via EFS-Web on Aug. 2, 2019, 12 pages.
"Final Office Action," for U.S. Appl. No. 15/840,540 dated Dec. 12, 2019 (22 pages).
"Final Office Action," for U.S. Appl. No. 15/994,263 dated Jan. 16, 2020 (29 pages).
"First Examination Report," for Indian Patent Application No. 201747029823 dated Nov. 25, 2019 (6 pages).
"First Office Action," for Chinese Patent Application No. 2016800187265 dated Nov. 5, 2019 (9 pages) with English Translation.
"Office Action," for Canadian Patent Application No. 2,836,266 dated Oct. 23, 2019 (3 pages).
"Office Action," for Japanese Patent Application No. 2017-540169 dated Nov. 21, 2019 (12 pages) with English Translation.
"Office Action," for Russian Patent Application No. 2017129933 dated Oct. 21, 2019 (9 pages) with English Translation.
"Response to Non-Final Office Action," for U.S. Appl. No. 15/840,540 filed with the USPTO dated Nov. 20, 2019 (13 pages).
"Written Submissions in Respect of Hearing on Nov. 14, 2019," for Indian Patent Application No. 3723/KOLNP/2013 filed Nov. 23, 2019 (19 pages).

DELIVERY OF HYDROPHOBIC ACTIVE AGENT PARTICLES

This application is a continuation of U.S. application Ser. No. 14/609,270, filed Jan. 29, 2015, which is a continuation-in-part application of U.S. application Ser. No. 13/793,390, filed Mar. 11, 2013, which is a continuation-in-part of U.S. application Ser. No. 13/469,844, filed May 11, 2012, now U.S. Pat. No. 9,757,497, issued Sep. 12, 2017, which claims the benefit of U.S. Provisional Application No. 61/488,582, filed May 20, 2011, the content of all of which is herein incorporated by reference.

FIELD OF THE INVENTION

The present invention relates to devices and coatings for devices such as medical device. More specifically, the present invention relates to devices and coatings for devices including hydrophobic active agent particles.

BACKGROUND OF THE INVENTION

The vascular system of the human is subject to blockage due to plaque within the arteries. Partial and even complete blockage of arteries by the formation of an atherosclerotic plaque is a well-known and frequent medical problem. Frequently, such blockage occurs in the coronary arteries. Blockages may also occur secondary to past treatment of specific sites (restenosis—such as that stemming from rapidly dividing smooth muscle cells). In addition, blockages can also occur in the context of peripheral arteries.

Blockages may be treated using atherectomy devices, which mechanically remove the plaque; hot or cold lasers, which vaporize the plaque; stents, which hold the artery open; and other devices and procedures designed to increase blood flow through the artery.

One common procedure for the treatment of blocked arteries is percutaneous transluminal coronary angioplasty (PTCA), also referred to as balloon angioplasty. In this procedure, a catheter having an inflatable balloon at its distal end is introduced into the coronary artery, the deflated, folded balloon is positioned at the stenotic site, and then the balloon is inflated. Inflation of the balloon disrupts and flattens the plaque against the arterial wall, and stretches the arterial wall, resulting in enlargement of the intraluminal passageway and increased blood flow. After such expansion, the balloon is deflated, and the balloon catheter removed. A similar procedure, called percutaneous transluminal angioplasty (PTA), is used in arteries other than coronary arteries in the vascular system. In other related procedures, a small mesh tube, referred to as a stent is implanted at the stenotic site to help maintain patency of the coronary artery. In rotoblation procedures, also called percutaneous transluminal rotational atherectomy (PCRA), a small, diamond-tipped, drill-like device is inserted into the affected artery by a catheterization procedure to remove fatty deposits or plaque. In a cutting balloon procedure, a balloon catheter with small blades is inflated to position the blades, score the plaque and compress the fatty matter into the artery wall. During one or more of these procedures, it may be desirable to deliver a therapeutic agent or drug to the area where the treatment is occurring to prevent restenosis, repair vessel dissections or small aneurysms or provide other desired therapy.

Additionally, it may be desirable to transfer therapeutic agents to other locations in a mammal, such as the skin, neurovasculature, nasal, oral, the lungs, the mucosa, sinus, the GI tract or the renal peripheral vasculature.

SUMMARY OF THE INVENTION

Embodiments of the invention include drug delivery coatings and devices including the same. In an embodiment, the invention includes a drug delivery coating including a polymeric layer. The polymeric layer can include a hydrophilic outer surface. The coating can also include a matrix contacting the hydrophilic outer surface. The matrix can include a particulate hydrophobic therapeutic agent and a cationic agent. The polymeric layer can further include a hydrophilic polymer having pendent photoreactive groups and a photo-crosslinker including two aryl ketone functionalities. Other embodiments are also included herein.

In an embodiment, the invention includes a drug delivery device including a substrate; a hydrophilic polymer layer disposed on the substrate; and coated therapeutic agent particles disposed on the hydrophilic polymer layer, the coated therapeutic agent particles comprising a particulate hydrophobic therapeutic agent; and a cationic agent disposed over the particulate hydrophobic therapeutic agent.

In an embodiment, the invention includes a drug delivery coating including a polymeric layer, the polymeric layer comprising a hydrophilic surface; coated therapeutic agent particles disposed on the hydrophilic surface, the coated therapeutic agent particles comprising a particulate hydrophobic therapeutic agent core; and a cationic agent surrounding the particulate hydrophobic therapeutic agent core, the cationic agent exhibiting affinity for the surface of a cell membrane.

In an embodiment, the invention includes a method of forming a drug delivery coating including applying a hydrophilic base coat onto a substrate; forming coated therapeutic agent particles, the coated therapeutic agent particles comprising a particulate hydrophobic therapeutic agent and a cationic agent disposed over the particulate hydrophobic therapeutic agent core; and applying the coated therapeutic agent particles to the substrate.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

Figure 1:
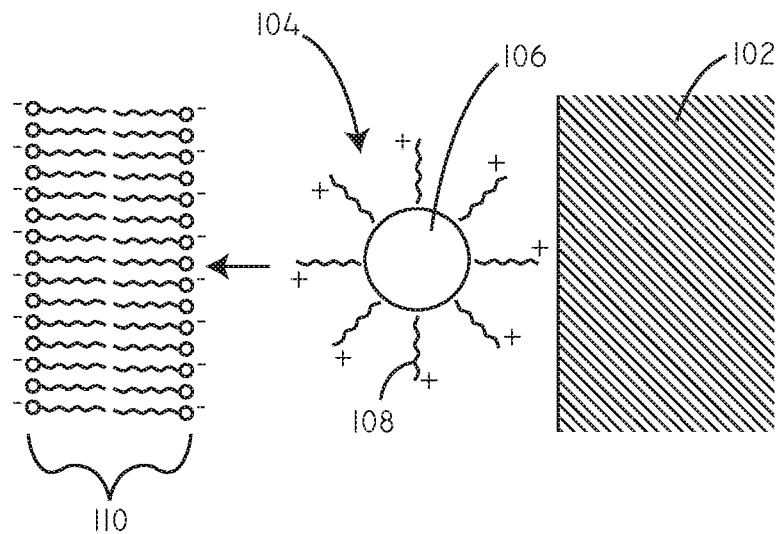
FIG. 1 is a schematic cross-sectional diagram of a coating in accordance with an embodiment herein.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As described above, in association with procedures such as percutaneous transluminal coronary angioplasty (PTCA), percutaneous transluminal angioplasty (PTA), and the like, it can be desirable to deliver a therapeutic agent or drug to the area where the treatment is occurring to prevent restenosis, repair vessel dissections or small aneurysms or provide other desired therapy. One approach for accomplishing this is to deliver a therapeutic agent (or active agent) to the desired tissue site using a drug delivery device such as a drug eluting balloon catheter or a drug-containing balloon catheter. Drug delivery coatings for certain medical applications desirably exhibit various properties. By way of example, in the context of a drug eluting balloon catheter or a drug-containing balloon catheter, the coating should maintain structural integrity during steps associated with preparation of the balloon catheter device include pleating, folding, and curing (such as heat treatment). In addition, it is desirable for the coating to maintain structural integrity during the process of passing through the vasculature through a catheter and/or over the guide wire, with limited loss of the active agent. Yet, it is also desirable upon inflation of the balloon at the desired site to transfer a substantial amount of the active agent from the balloon and onto the vessel wall. In addition, it is desirable to maximize uptake of the active agent into the tissue of the of the vessel wall and reduce the amount of active agent that is washed away into the blood flowing through the treatment site in the vasculature.

Embodiments herein can be useful to enhance one or more desirable properties of drug delivery coatings, such as those properties desirable in the context of drug eluting balloon catheters, drug-containing balloon catheters and similar devices. In various embodiments, a drug delivery device is provided that includes a substrate and coated therapeutic agent particles disposed on the substrate. The coated therapeutic agent particles can include a particulate hydrophobic therapeutic agent and a cationic agent disposed over the particulate hydrophobic therapeutic agent.

Referring now to FIG. 1, a schematic cross-sectional diagram (not to scale) is provided of a coating in accordance with an embodiment herein. In this embodiment, coated therapeutic agent particles 104 are disposed on a substrate 102. Exemplary substrates are described in greater detail below. The coated therapeutic agent particles 104 can include a plurality of cationic agents 108 disposed over a particulate hydrophobic therapeutic agent 106. The coated therapeutic agent particles 104 can be contiguously coated with cationic agents 108. In other embodiments, the cationic agent 108 coating on the therapeutic agent particles 104 can be discontinuous. Additionally, the particulate hydrophobic agents 106 can coexist in a matrix with cationic agents 108 wherein the cationic agent 108 does not coat the particulate hydrophobic agent 106. Various mixtures of the embodiments described above can be found on a specific substrate 102. For example, but not limiting, a coating on a substrate can include coated therapeutic agent particles 104 contiguously coated with cationic agents 108 and particulate hydrophobic agents 106 in a matrix with cationic agents 108 wherein the cationic agent 108 does not coat the particulate hydrophobic agent 106. It will be appreciated that as actually applied there will be many hydrophobic therapeutic agent particulates within a given coating and that a single particulate is shown in FIG. 1 just for purposes of ease of illustration. Exemplary cationic agents and hydrophobic therapeutic agents are described in greater detail below. The charge provided by the cationic agents 108 can be electrostatically attracted to negative charges and/or polar groups associated with the lipid bilayer 110 of a cell membrane and cellular components within the lipid bilayer 110.

Figure 2:
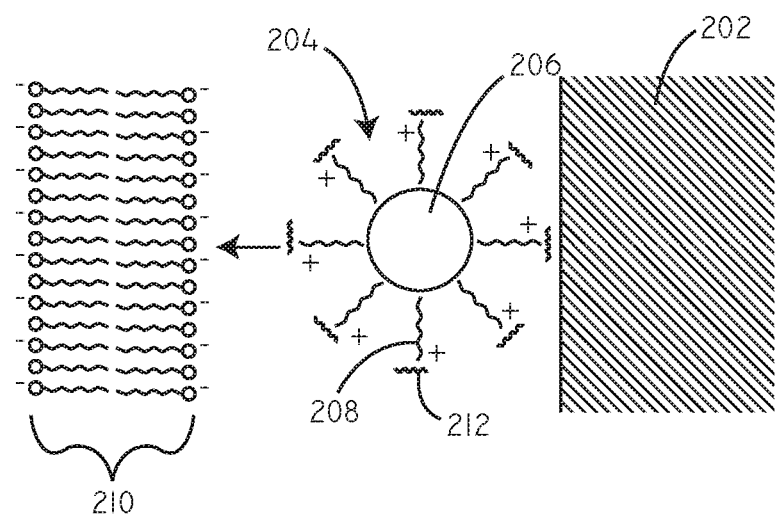
FIG. 2 is a schematic cross-sectional diagram of a coating in accordance with an embodiment herein.

In some embodiments, nucleic acids may also be included in coatings herein. By way of example, nucleic acids, including but not limited to siRNA, may be associated with the cationic agent. Exemplary nucleic acids are described in greater detail below. Referring now to FIG. 2, a schematic cross-sectional diagram (not to scale) is provided of another embodiment herein. In this embodiment, coated therapeutic agent particles 204 are disposed on a substrate 202. The coated therapeutic agent particles 204 can include a plurality of cationic agents 208 disposed over a particulate hydrophobic therapeutic agent 206. Nucleic acids 212 can be associated with the cationic agent. The charge provided by the cationic agents 208 can be electrostatically attracted to negative charges and/or polar groups associated with the lipid bilayer 210 of a cell membrane and cellular components within the lipid bilayer 210.

Figure 3:
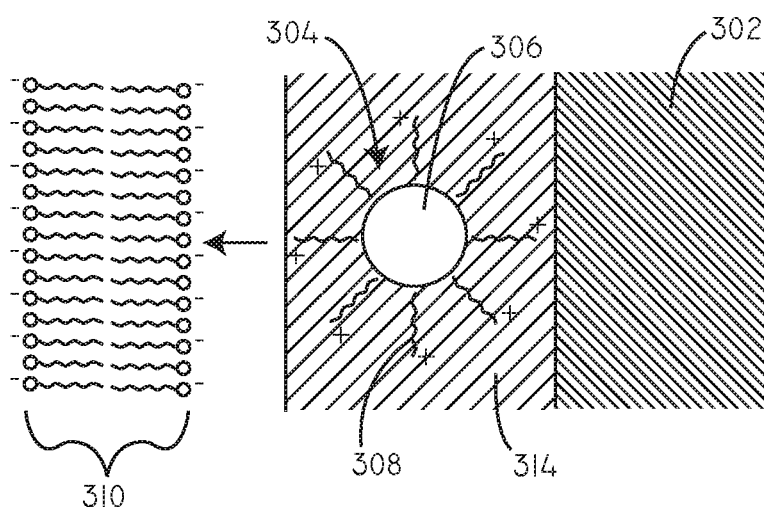
FIG. 3 is a schematic cross-sectional diagram of a coating in accordance with an embodiment herein.

In some embodiments, an additive may be included along with the coated therapeutic agent particles 304 in coatings herein. Referring now to FIG. 3, a schematic cross-sectional diagram (not to scale) is provided of another embodiment. In this embodiment, coated therapeutic agent particles 304 are disposed on a substrate 302. An additive 314 can be disposed along with the coated therapeutic agent particles 304. The amount of the additive 314 can be more than, less than, or equal to the amount of the coated therapeutic agent particles 304. In some embodiments, the additive 314 can form a matrix or layer in which the coated therapeutic agent particles 304 are disposed. In various embodiments, the additive can be hydrophilic. Exemplary additive components are described in greater detail below. The coated therapeutic agent particles 304 can include a plurality of cationic agents 308 disposed over a particulate hydrophobic therapeutic agent 306. The charge provided by the cationic agents 308 can be electrostatically attracted to negative charges and/or polar groups associated with the lipid bilayer 310 of a cell membrane and cellular components within the lipid bilayer 310.

Figure 4:
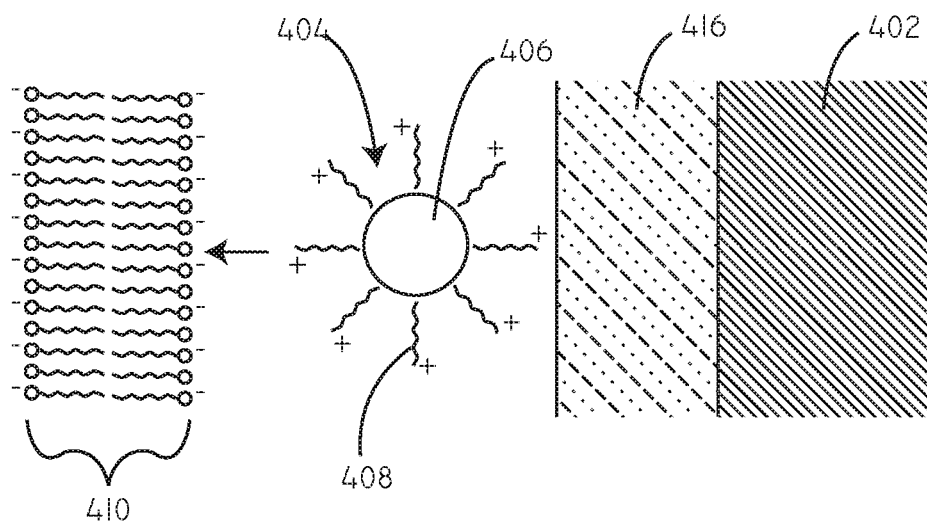
FIG. 4 is a schematic cross-sectional diagram of a coating in accordance with an embodiment herein.

In some embodiments, a hydrophilic polymer layer can be disposed on the surface of the substrate, between the coated therapeutic agent particles and the surface of the substrate. Exemplary polymers for the hydrophilic polymer layer are described in greater detail below. Referring now to FIG. 4, a schematic cross-sectional diagram (not to scale) is provided of another embodiment herein. In this embodiment, coated therapeutic agent particles 404 are disposed on a hydrophilic polymer layer 416, which is in turn disposed on a substrate 402. The coated therapeutic agent particles 404 can include a plurality of cationic agents 408 disposed over a particulate hydrophobic therapeutic agent 406. The charge provided by the cationic agents 408 can be electrostatically attracted to negative charges and/or polar groups associated with the lipid bilayer 410 of a cell membrane and cellular components within the lipid bilayer 410.

Figure 5:
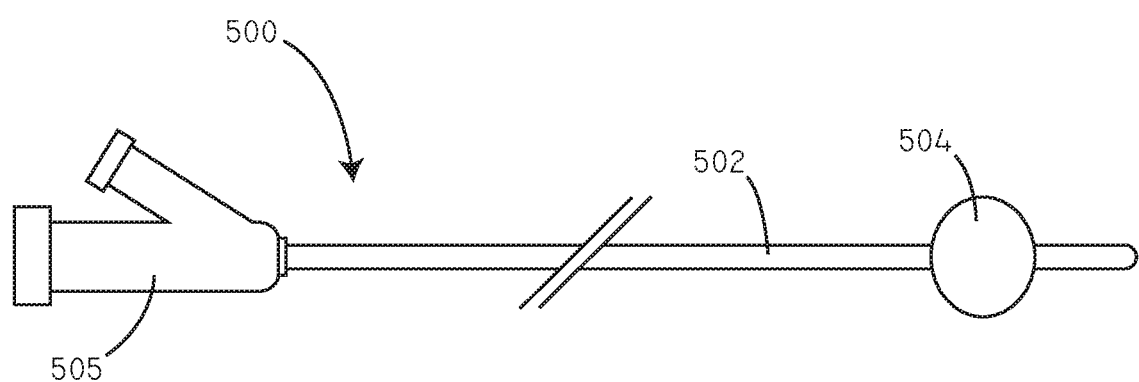
FIG. 5 is a schematic diagram of a device in accordance with an embodiment herein.

Referring now to FIG. 5, a schematic view of an exemplary device is shown in accordance with an embodiment. The device 500 can be, for example, an angioplasty balloon catheter or a drug eluting balloon catheter or a drug-containing balloon catheter. However, further examples of exemplary devices are described in greater detail below. The device 500 includes a catheter shaft 502 and a manifold end 505. The device 500 also includes an inflatable balloon 504 disposed around the catheter shaft 502. In FIG. 5, the balloon 504 is shown in an inflated configuration. The catheter shaft 502 can include a channel to convey fluid through the catheter shaft 502 and to or from the balloon 504, so that the balloon 504 can selectively go from a deflated configuration to the inflated configuration and back again.

The manufacture of expandable balloons is well known in the art, and any suitable process can be carried out to provide the expandable substrate portion of the insertable medical device as described herein. Catheter balloon construction is described in various references, for example, U.S. Pat. Nos. 4,490,421, 5,556,383, 6,210,364, 6,168,748, 6,328,710, and 6,482,348. Molding processes are typically performed for balloon construction. In an exemplary molding process, an extruded polymeric tube is radially and axially expanded at elevated temperatures within a mold having the desired shape of the balloon. The balloon can be subjected to additional treatments following the molding process. For example, the formed balloon can be subjected to additional heating steps to reduce shrinkage of the balloon.

Referring back to FIG. 5, the insertable medical device 500 can also have one or more non-expandable (or inelastic) portions. For example, in a balloon catheter, the catheter shaft 502 portion can be the non-expandable portion. The non-expandable portion can be partially or entirely fabricated from a polymer. Polymers include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, polyamides such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone. The non-expandable portion can also be partially or entirely fabricated from a metal.

Figure 6:
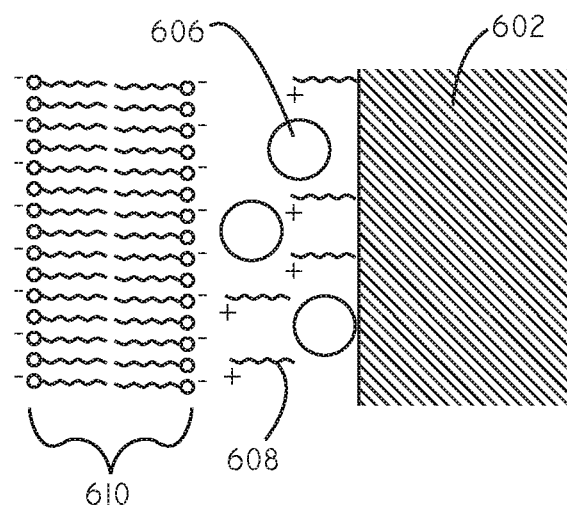
FIG. 6 is a schematic cross-sectional diagram of a coating in accordance with various embodiments herein.

Referring now to FIG. 6, a schematic cross-sectional diagram (not to scale) is provided of a drug delivery coating in accordance with various embodiments herein. In this embodiment, particulate hydrophobic therapeutic agents 606 are disposed on a substrate 602. Exemplary substrates are described in greater detail below. A plurality of cationic agents 608 are also disposed on the substrate. The particulate hydrophobic therapeutic agents 606 and the cationic agents 608 can form a matrix. It will be appreciated that as actually applied there can be many more hydrophobic therapeutic agent particulates within a given matrix. Exemplary cationic agents and hydrophobic therapeutic agents are described in greater detail below. The charge provided by the cationic agents 608 can be electrostatically attracted to negative charges and/or polar groups associated with the lipid bilayer 610 of a cell membrane and cellular components within the lipid bilayer 610.

Figure 7:
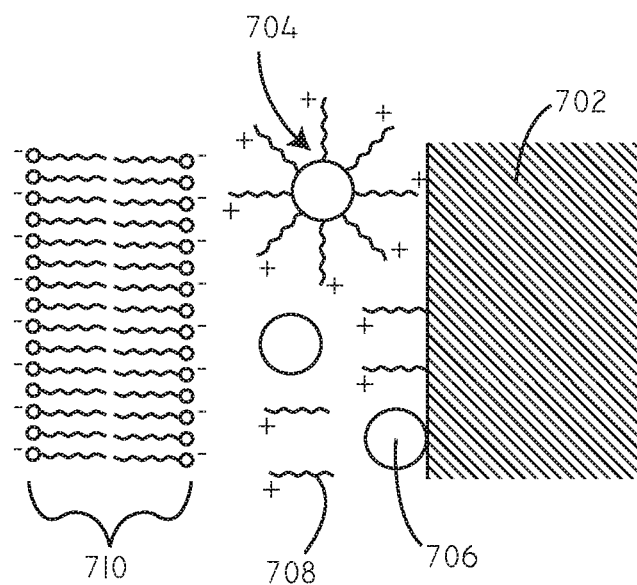
FIG. 7 is a schematic cross-sectional diagram of a coating in accordance with various embodiments herein.

Referring now to FIG. 7, a schematic cross-sectional diagram (not to scale) is provided of a drug delivery coating in accordance with various embodiments herein. In this embodiment, particulate hydrophobic therapeutic agents 706 are disposed on a substrate 702. A plurality of cationic agents 708 are also disposed on the substrate. The particulate hydrophobic therapeutic agents 706 and the cationic agents 708 can form a matrix. The particulate hydrophobic therapeutic agents 706 and the cationic agents 708 can be associated with one another and in some cases can form coated therapeutic agent particles 704 disposed on the substrate 702. The coated therapeutic agent particles 704 can include a plurality of cationic agents 708 disposed over a particulate hydrophobic therapeutic agent 706. It will be appreciated that as actually applied there can be many hydrophobic therapeutic agent particulates within a given coating and that particulates shown in FIG. 7 are just for purposes of ease of illustration. The charge provided by the cationic agents 708 can be electrostatically attracted to negative charges and/or polar groups associated with the lipid bilayer 710 of a cell membrane and cellular components within the lipid bilayer 710.

Figure 8:
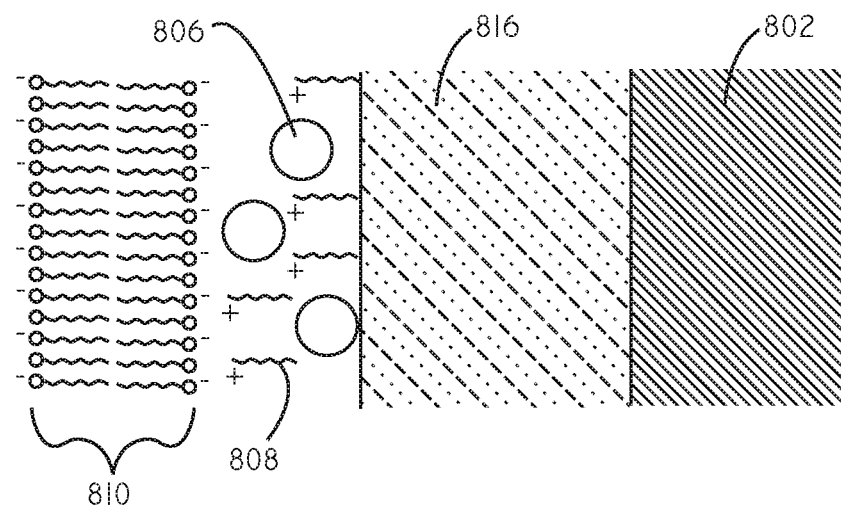
FIG. 8 is a schematic cross-sectional diagram of a coating in accordance with various embodiments herein.

In some embodiments, a hydrophilic polymer layer can be disposed on the surface of the substrate, between the therapeutic agent, cationic agent, and/or coated therapeutic agent particles and the surface of the substrate. Exemplary polymers for the hydrophilic polymer layer are described in greater detail below. Referring now to FIG. 8, a schematic cross-sectional diagram (not to scale) is provided of a drug delivery coating in accordance with various embodiments herein. A hydrophilic polymer layer 816 is disposed on a substrate 802. Particulate hydrophobic therapeutic agents 806 are disposed on the hydrophilic polymer layer 816. A plurality of cationic agents 808 can also be disposed on the hydrophilic polymer layer 816. The particulate hydrophobic therapeutic agents 806 and the cationic agents 808 can be associated with one another. The particulate hydrophobic therapeutic agents 806 and the cationic agents 808 can form a matrix. The charge provided by the cationic agents 808 can be electrostatically attracted to negative charges and/or polar groups associated with the lipid bilayer 810 of a cell membrane and cellular components within the lipid bilayer 810.

Figure 9:
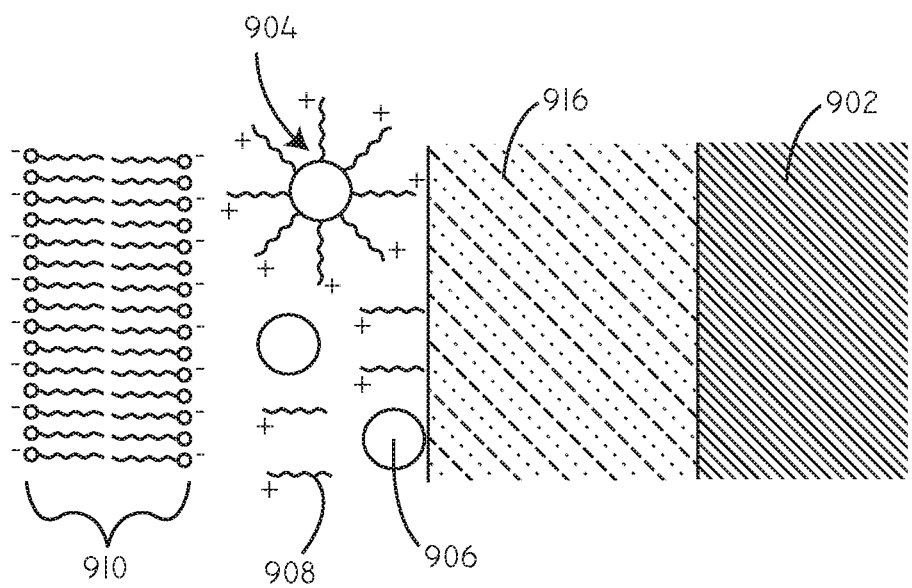
FIG. 9 is a schematic cross-sectional diagram of a coating in accordance with various embodiments herein.

Referring now to FIG. 9, a schematic cross-sectional diagram (not to scale) is provided of a drug delivery coating in accordance with various embodiments herein. A hydrophilic polymer layer 916 is disposed on a substrate 902. Particulate hydrophobic therapeutic agents 906 can be disposed on the hydrophilic polymer layer 916. A plurality of cationic agents 908 can also disposed on the hydrophilic polymer layer 916. The particulate hydrophobic therapeutic agents 906 and the cationic agents 908 can form a matrix. The particulate hydrophobic therapeutic agents 906 and the cationic agents 908 can be associated with one another and in some cases can form coated therapeutic agent particles 904 disposed on the hydrophilic polymer layer 916. The coated therapeutic agent particles 904 can include a plurality of cationic agents 908 disposed over a particulate hydrophobic therapeutic agent 906. The charge provided by the cationic agents 908 can be electrostatically attracted to negative charges and/or polar groups associated with the lipid bilayer 910 of a cell membrane and cellular components within the lipid bilayer 910.

Cationic Agents

Cationic agents used in embodiments herein can include compounds containing a portion having a positive charge in aqueous solution at neutral pH along with a portion that can exhibit affinity for hydrophobic surfaces (such as hydrophobic or amphiphilic properties) and can therefore interface with hydrophobic active agents. In some embodiments, cationic agents used in embodiments herein can include those having the general formula X—Y, wherein X is a radical including a positively charged group in aqueous solution at neutral pH and Y is a radical exhibiting hydrophobic properties. In some embodiments, the cationic agent can include a hydrophilic head and a hydrophobic tail, along with one or more positively charged groups, typically in the area of the hydrophilic head.

Cationic agents of the present disclosure can include salts of cationic agents at various pH ranges, such as, but not limited to, halide salts, sulfate salts, carbonate salts, nitrate salts, phosphate salts, acetate salts and mixtures thereof.

Cationic agents can specifically include cationic lipids and net neutral lipids that have a cationic group (neutral lipids with cationic groups). Exemplary lipids can include, but are not limited to, 3ß[N—(N',N'-dimethylaminoethane)-carbamoyl]cholesterol hydrochloride (DC-cholesterol); 1,2-dioleoyl-3-trimethylammonium-propane (DOTAP); dimethyldioctadecylammonium (DDAB); 1,2-dioleoyl-sn-glycero-3-ethylphosphocholine (EPC); 1,2-di-O-octadecenyl-3-trimethylammonium propane (DOTMA); 1,2-di-(9Z-octadecenoyl)-3-dimethylammonium-propane (DODAP); 1,2-dilinoleyloxy-3-dimethylaminopropane (DLinDMA) and derivatives thereof. Additional lipids can include, but are not limited to, 1,2-dioleoyl-sn-glycero-3-phosphoethanolamine (DOPE); cholesterol; 1,2-dioctadecanoyl-sn-glycero-3-phosphocholine (DSPC); 1,2-distearoyl-sn-glycero-3-phosphoethanolamine (DSPE). Other cationic agents can include mono- or polyaminoalkanes such as spermine and spermidine.

Cationic agents can specifically include cationic polymers. Cationic agents can also include polycation-containing cyclodextrin (for example, but not limited to, amino cyclodextrin and derivatives thereof), amino dextran, histones, protamines, cationized human serum albumin, aminopolysaccharides such as chitosan, peptides such as poly-L-lysine, poly-L-ornithine, and poly(4-hydroxy-L-proline ester, and polyamines such as polyethylenimine (PEI; available from Sigma Aldrich), polyallylamine, polypropylenimine, polyamidoamine dendrimers (PAMAM; available from Sigma Aldrich), cationic polyoxazoline and poly(beta-aminoesters). Cationic agents can also specifically include cationic lipidoids (as described by K. T. Love in the publication PNAS 107, 1864-1869 (2010)). Other exemplary cationic polymers include, but are not limited to, block copolymers such as PEG-PEI and PLGA-PEI copolymers. Other exemplary cationic agents include positively charged gelatin (for example, base-treated gelatin), and the family of aminated cucurbit[n]urils (wherein n=5, 6, 7, 8, 10).

In other embodiments of the present disclosure, cationic agents containing a portion having a positive charge in aqueous solutions at neutral pH include the following Compounds (A-I):

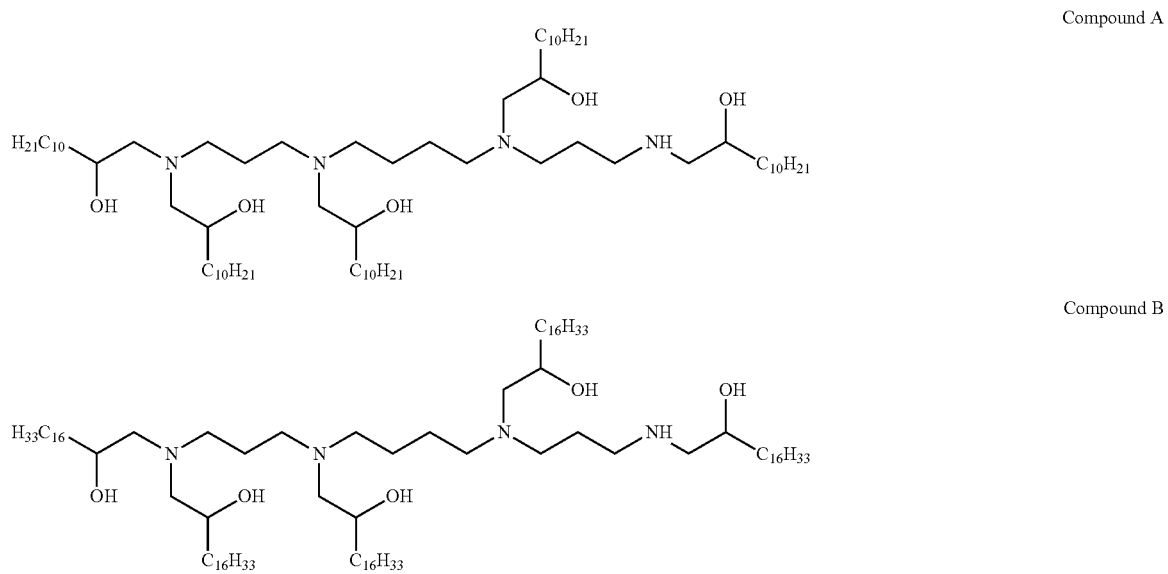

Compound A

Compound B

-continued

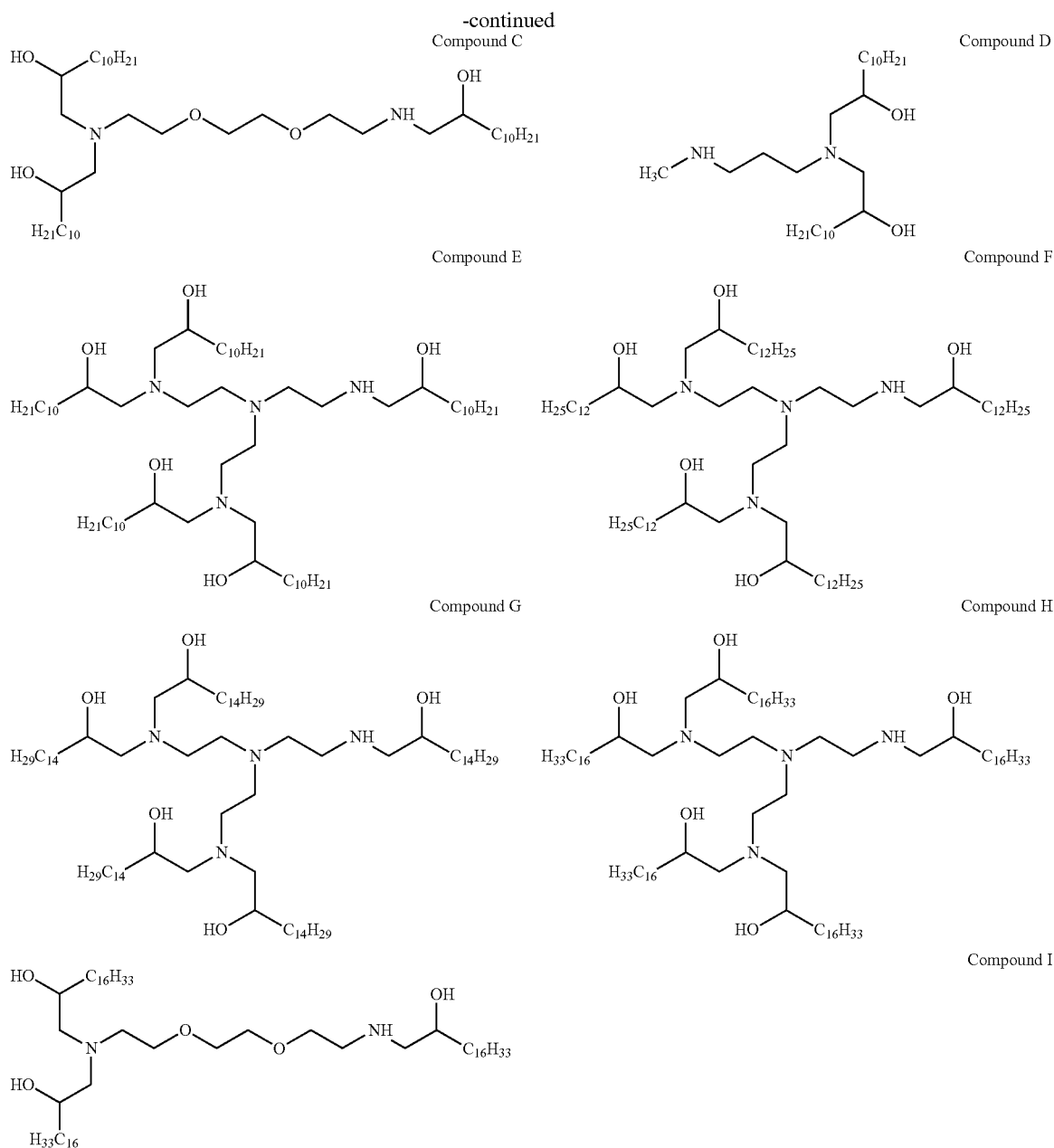

Additionally, other cationic agents include structures of the general Formula I:

TABLE 1

Values for Variables x + z, y and R for Compounds J-R of Formula I.

| Compound | x + z | y | R |
| --- | --- | --- | --- |
| Compound J | 6 | 12.5 | $C_{12}H_{25}$ |
| Compound K | 1.2 | 2 | $C_{12}H_{25}$ |
| Compound L | 6 | 39 | $C_{12}H_{25}$ |
| Compound M | 6 | 12.5 | $C_{14}H_{29}$ |
| Compound N | 1.2 | 2 | $C_{14}H_{29}$ |
| Compound O | 6 | 39 | $C_{14}H_{29}$ |
| Compound P | 6 | 12.5 | $C_{16}H_{33}$ |
| Compound Q | 1.2 | 2 | $C_{16}H_{33}$ |
| Compound R | 6 | 39 | $C_{16}H_{33}$ |

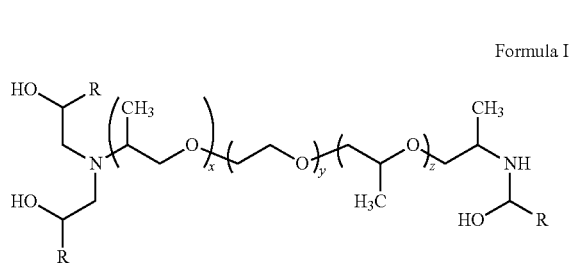

Formula I

Cationic agents, such as those listed above, can generally be prepared by the reaction of an appropriate hydrophobic epoxide (e.g. oleyl epoxide) with a multifunctional amine (e.g. propylene diamine). Details of the synthesis of related cationic agents are described by K. T. Love in the publication PNAS 107, 1864-1869 (2010) and Ghonaim et al., Pharma Res 27, 17-29 (2010).

It will be appreciated that polyamide derivatives of PEI (PEI-amides) can also be applied as cationic agents. PEI-amides can generally be prepared by reacting PEI with an acid or acid derivative such as an acid chloride or an ester to form various PEI-amides. For example, PEI can be reacted with methyl oleate to form PEI-amides.

In yet other embodiments cationic agents can include moieties used to condense nucleic acids (for example lipids, peptides and other cationic polymers). In some instances these cationic agents can be used to form lipoplexes and polyplexes.

Exemplary embodiments of cationic agents can also include, but are not limited to, cationic agent derivatives that are photo reactive. Photo reactive groups are described below. Such cationic agent derivatives include PEI polymer derivatives of benzophenone and PAMAM polymer derivatives of benzophenone.

In some embodiments, the molecular weight of the cationic agent can be about 1.2 kDa, 2.5 kDa, 10 kDa, 25 kDa, 250 kDa or even, in some cases, 750 kDa. In yet other embodiments the molecular weight of the cationic agent can be in the range of 50-100 kDa, 70-100 kDa, 50-250 kDa, 25-100 kDa, 2.5-750 kDa or even, in some cases, 2.5-2,000 kDa. Other embodiments include molecular weights greater than 1.2 kDa, 2.5 kDa, 10 kDa, 25 kDa, 250 kDa or even, in some cases, greater than 750 kDa. Other embodiments can include cationic agents up to 2,000 kDa.

Low molecular weight cationic agent monomers or low molecular weight cationic oligomers can be combined with hydrophobic active agent to produce a reactive coating. These reactive coatings can then be coated onto a substrate and thermally polymerized or polymerized with UV-radiation. Exemplary monomers include, but are not limited to, aziridine, vinylamine, allylamine and oligomers from 80 g/mol to 1200 g/mol. Crosslinkers (e.g., 1,2-dichloroethane, epichlorohydrin, 1,6-diisocyanatohexane) could be used to crosslink oligomers.

Additive Components

In some embodiments of the present disclosure the additive components can be hydrophilic in nature. Exemplary hydrophilic polymers include, but are not limited to, PEG, PVP and PVA.

Exemplary additive components can include saccharides. Saccharides can include monosaccharides, disaccharides, trisaccharides, oligosaccharides, and polysaccharides. Polysaccharides can be linear or branched polysaccharides. Exemplary saccharides can include but are not limited to dextrose, sucrose, maltose, mannose, trehalose, and the like. Exemplary saccharides can further include, but are not limited to, polysaccharides including pentose, and/or hexose subunits, specifically including glucans such as glycogen and amylopectin, and dextrins including maltodextrins, fructose, mannose, galactose, and the like. Polysaccharides can also include gums such as pullulan, arabinose, galactan, etc.

Saccharides can also include derivatives of polysaccharides. It will be appreciated that polysaccharides include a variety of functional groups that can serve as attachment points or can otherwise be chemically modified in order to alter characteristics of the saccharide. As one example, it will be appreciated that saccharide backbones generally include substantial numbers of hydroxyl groups that can be utilized to derivatize the saccharide.

Saccharides can also include copolymers and/or terpolymers, and the like, that include saccharide and/or saccharide subunits and/or blocks.

Polysaccharides used with embodiments herein can have various molecular weights. By way of example, glycogen used with embodiments herein can have a molecular weight of greater than about 250,000. In some embodiments glycogen used with embodiments herein can have a molecular weight of between about 100,000 and 10,000,000 Daltons.

Refinement of the molecular weight of polysaccharides can be carried out using diafiltration. Diafiltration of polysaccharides such as maltodextrin can be carried out using ultrafiltration membranes with different pore sizes. As an example, use of one or more cassettes with molecular weight cut-off membranes in the range of about 1K to about 500 K can be used in a diafiltration process to provide polysaccharide preparations with average molecular weights in the range of less than 500 kDa, in the range of about 100 kDa to about 500 kDa, in the range of about 5 kDa to about 30 kDa, in the range of about 30 kDa to about 100 kDa, in the range of about 10 kDa to about 30 kDa, or in the range of about 1 kDa to about 10 kDa.

It will be appreciated that polysaccharides such as maltodextrin and amylose of various molecular weights are commercially available from a number of different sources. For example, Glucidex™ 6 (avg. molecular weight ~95,000 Da) and Glucidex™ 2 (avg. molecular weight ~300,000 Da) are available from Roquette (France); and MALTRIN™ maltodextrins of various molecular weights, including molecular weights from about 12,000 Da to 15,000 Da are available from GPC (Muscatine, Iowa). Examples of other hydrophobic polysaccharide derivatives are disclosed in US Patent Publication 2007/0260054 (Chudzik), which is incorporated herein by reference.

Exemplary additive components can include amphiphilic compounds. Amphiphilic compounds include those having a relatively hydrophobic portion and a relatively hydrophilic portion. Exemplary amphiphilic compounds can include, but are not limited to, polymers including, at least blocks of, polyvinylpyrrolidone, polyvinyl alcohol, polyethylene glycol, polyoxazolines (such as poly(2-alkyloxazoline) and derivatives) and the like. Exemplary amphiphilic compounds can specifically include poloxamers. Poloxamers are nonionic triblock copolymers composed of a central hydrophobic chain of polyoxypropylene flanked by two hydrophilic chains of polyoxyethylene. Poloxamers are frequently referred to by the trade name PLURONIC®. It will be appreciated that many aspects of the copolymer can be varied such the characteristics can be customized. One exemplary poloxamer is PLURONIC® F68 (non-ionic, copolymer of ethylene and propylene oxide commercially available from BASF Corporation; also designated as F68 and poloxamer F68), which refers to a poloxamer having a solid form at room temperature, a polyoxypropylene molecular mass of approximately 1,800 g/mol and roughly 80% polyoxyethylene content, with a total molecular weight of approximately 8,400 g/mol, the copolymer terminating in primary hydroxyl groups.

Exemplary additive components can further include compounds that stabilize poorly water soluble pharmaceutical agents. Exemplary additive components providing such stabilization include biocompatible polymers, for example albumins. Additional additive components are described in U.S. Pat. No. 7,034,765 (De et al.), the disclosure of which is incorporated herein by reference. Stabilization of suspensions and emulsions can also be provided by compounds, for example, such as surfactants (e.g. F68).

Various additive components can be added as an optional topcoat over the layer containing the hydrophobic active agent. In some embodiments, the topcoat can be applied to modify the release characteristic of the hydrophobic active agent. Other topcoats can be added as a protection layer to reduce inadvertent loss of the hydrophobic active agent through friction or general wear. For example, the topcoat can act as a protection layer for handling purposes during packaging or to protect the hydrophobic active agent until the hydrophobic active can be delivered to the target site in the body, or both. For example, the optional topcoat can include polyvinylpyrrolidone (PVP), polyacrylic acid (PAA), and polyurethane.

Hydrophobic Active Agents

It will be appreciated that hydrophobic active agents of embodiments herein (e.g., particulate hydrophobic therapeutic agents), can include agents having many different types of activities. The terms "active agent" and "therapeutic agent" as used herein shall be coterminous unless the context dictates otherwise. Hydrophobic active agents can specifically include those having solubility in water of less than about 100 µg/mL at 25 degrees Celsius and neutral pH. In various embodiments, hydrophobic active agents can specifically include those having solubility in water of less than about 10 µg/mL at 25 degrees Celsius and neutral pH. In some embodiments, hydrophobic active agents can specifically include those having solubility in water of less than about 5 µg/ml at 25 degrees Celsius and neutral pH.

In some exemplary embodiments, active agents can include, but are not limited to, antiproliferatives such as paclitaxel, sirolimus (rapamycin), zotarolimus, everolimus, temsirolimus, pimecrolimus, tacrolimus, and ridaforolimus; analgesics and anti-inflammatory agents such as aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxyphenbutazone, phenylbutazone, piroxicam, sulindac; anti-arrhythmic agents such as amiodarone HCl, disopyramide, flecainide acetate, quinidine sulphate; anti-bacterial agents such as benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim; anti-coagulants such as dicoumarol, dipyridamole, nicoumalone, phenindione; anti-hypertensive agents such as amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL; anti-muscarinic agents: atropine, benzhexol HCl, biperiden, ethopropazine HCl, hyoscyamine, mepenzolate bromide, oxyphencyclimine HCl, tropicamide; anti-neoplastic agents and immunosuppressants such as aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone; beta-blockers such as acebutolol, alprenolol, atenolol, labetalol, metoprolol, nadolol, oxprenolol, pindolol, propranolol; cardiac inotropic agents such as amrinone, digitoxin, digoxin, enoximone, lanatoside C, medigoxin; corticosteroids such as beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone; lipid regulating agents such as bezafibrate, clofibrate, fenofibrate, gemfibrozil, probucol; nitrates and other anti-anginal agents such as amyl nitrate, glyceryl trinitrate, isosorbide dinitrate, isosorbide mononitrate, pentaerythritol tetranitrate.

Other exemplary embodiments of active agents include, but are not limited to, active agents for treatment of hypertension (HTN), such as guanethidine.

In a particular embodiment, the hydrophobic active agents are selected from the group consisting of paclitaxel, sirolimus (rapamycin) and mixtures thereof.

In some embodiments, a hydrophobic active agents can be conjugated to a cationic agent. The conjugation can include a hydrophobic active agent covalently bonded to the cationic agent. In some embodiments wherein the hydrophobic agent is conjugated to the cationic agent a linking agent can be used to attach the hydrophobic agent to the cationic agent. Suitable linking agents include, but are not limited to, polyethylene glycol, polyethylene oxide and polypeptides of naturally-occurring and non-naturally occurring amino acids. In some embodiments, linking agents can be biodegradable or cleavable in vivo to assist in release of the hydrophobic active agents. Exemplary linking agents can further include alkane or aromatic compounds with heteroatom-substitutions such as N, S, Si, Se or O.

Particle size and size distribution of a particulate preparation can be determined using any one of various techniques known in the art. In one mode of practice, laser diffraction can be used to measure particle size and distribution. In laser diffraction a laser beam passes through a dispersed particulate sample and angular variation in intensity of light scattered is measured. The angle of light scattering is greater for large particles and less for smaller particles, and the angular scattering intensity data can be collected and analyzed to generate a particle size profile.

Analysis of particulate size and distribution can be performed using laser light scattering equipment such as Malvern System 4700, (for particles from 1 nm to 3 µm) or Horiba LA-930 (e.g., for particles from 100 nm to 2 mm). The output from such analyzers can provide information on the sizes of individual particulates, and the overall amount of particulates of these sizes reflecting the distribution of particulates in terms of size. Analysis providing data on the size distribution can be provided in the form of a histogram, graphically representing the size and size distribution of all the particulates in a preparation.

Exemplary particulate hydrophobic therapeutic agents can have different morphological characteristics. In some embodiments the particulate hydrophobic therapeutic agent can be crystalline. In yet other embodiments of the present disclosure the particulate hydrophobic therapeutic agent can be amorphous. Additionally, combinations of crystalline and amorphous particulate hydrophobic therapeutic agents can be desirable in order to achieve, for example, desired solubilities of the particulate hydrophobic therapeutic agents.

In some embodiments, the particulate hydrophobic therapeutic agent can have an average diameter ("dn", number average) that is less than about 30 µm or less than about 10 µm. Also, in some embodiments, the particulate hydrophobic therapeutic agent can have an average diameter of about 100 nm or larger. For example, the microparticulates associated with the expandable elastic portion can have an average diameter in the range of about 100 nm to about 10

μm, about 150 nm to about 2 μm, about 200 nm to about 5 μm, or even about 0.3 μm to about 1 μm.

Nucleic Acids

Nucleic acids used with embodiments of the invention can include various types of nucleic acids that can function to provide a therapeutic effect. Exemplary types of nucleic acids can include, but are not limited to, ribonucleic acids (RNA), deoxyribonucleic acids (DNA), small interfering RNA (siRNA), micro RNA (miRNA), piwi-interacting RNA (piRNA), short hairpin RNA (shRNA), antisense nucleic acids, aptamers, ribozymes, locked nucleic acids and catalytic DNA. In a particular embodiment, the nucleic acid used is siRNA and/or derivatives thereof.

In some exemplary embodiments of the present disclosure, the range of the percent ratio of hydrophobic active agent to cationic agent (e.g. % PTX/% PEI or % PTX/% DOTAP; wt/wt) is from about 99.9/0.1 to about 70/30. In yet other embodiments it can be appreciated that the range of the percent ratio of hydrophobic active agents is from about 99/1 to about 73/27; from about 98/2 to about 75/25; from about 98/2 to about 86/14; from about 97/3 to about 88/12; from about 95/5 to about 90/10; and even in some exemplary embodiments from about 93/7 to about 91/9.

Hydrophilic Base Coatings

One class of hydrophilic polymers useful as polymeric materials for hydrophilic base coat formation is synthetic hydrophilic polymers. Synthetic hydrophilic polymers that are biostable (i.e., that show no appreciable degradation in vivo) can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these. Examples of polymers that can be formed from these monomers include poly(acrylamide), poly(methacrylamide), poly(vinylpyrrolidone), poly(acrylic acid), poly(ethylene glycol), poly(vinyl alcohol), and poly (HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,Ndimethylacrylamide-co-aminopropylmethacrylamide) and poly(acrylamide-co-N,Ndimethylaminopropylmethacrylamide) are described in example 2 of U.S. Pat. No. 7,807,750 (Taton et al.), the disclosure of which is incorporated herein by reference.

Other hydrophilic polymers that can be useful in the present disclosure are derivatives of acrylamide polymers with photoreactive groups. One such representative hydrophilic polymer can be the copolymerization of N-[3-(4-benzoylbenzamido)propyl]methacrylamide (Formula I) with N-(3-aminopropyl)methacrylamide (Formula II) to produce the polymer poly(N-3-aminopropyl)methacrylamide-co-N-[3-(4-benzoylbenzamido)propyl]methacrylamide (Formula III). The preparation of the polymer is disclosed in Example 1 of US Patent Publication 2007/0032882 (to Lodhi, et al.), the full content of which is incorporated herein by reference.

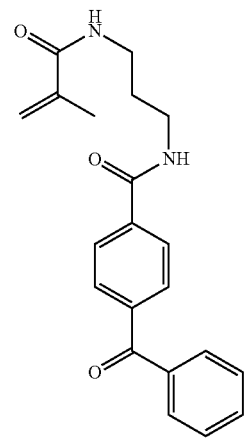
Formula I

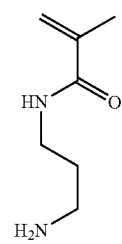
Formula II

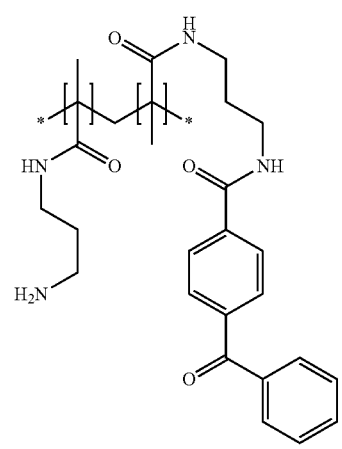
Formula III

In some embodiments, the hydrophilic polymer can be a vinyl pyrrolidone polymer, or a vinyl pyrrolidone/(meth) acrylamide copolymer such as poly(vinylpyrrolidone-co-methacrylamide). If a PVP copolymer is used, it can be a copolymer of vinylpyrrolidone and a monomer selected from the group of acrylamide monomers. Exemplary acrylamide monomers include (meth)acrylamide and (meth) acrylamide derivatives, such as alkyl(meth)acrylamide, as exemplified by dimethylacrylamide, and aminoalkyl(meth) acrylamide, as exemplified by aminopropylmethacrylamide and dimethylaminopropylmethacrylamide. For example, poly(vinylpyrrolidone-co-N,N dimethylaminopropylmethacrylamide) is described in example 2 of U.S. Pat. No. 7,807,750 (Taton et al.).

In one embodiment, the polymers and copolymers as described are derivatized with one or more photoactivatable group(s). Exemplary photoreactive groups that can be pendent from biostable hydrophilic polymer include aryl ketones, such as acetophenone, benzophenone, anthraquinone, anthrone, quinone, and anthrone-like heterocycles.

Aryl ketones herein can specifically include diaryl ketones. Polymers herein can provide a hydrophilic polymer having a pendent activatable photogroup that can be applied to the expandable and collapsible structure, and can then treated with actinic radiation sufficient to activate the photogroups and cause covalent bonding to a target, such as the material of the expandable and collapsible structure. Use of photo-hydrophilic polymers can be used to provide a durable coating of a flexible hydrogel matrix, with the hydrophilic polymeric materials covalently bonded to the material of the expandable and collapsible structure.

A hydrophilic polymer having pendent photoreactive groups can be used to prepare the flexible hydrogel coating. Methods of preparing hydrophilic polymers having photoreactive groups are known in the art. For example, methods for the preparation of photo-PVP are described in U.S. Pat. No. 5,414,075, the disclosure of which is incorporated herein by reference. Hydrophilic photo-polyacrylamide polymers such as poly(acrylamide-co-N-(3-(4-benzoylbenzamido)propyl)methacylamide), "Photo-PAA", and derivatives thereof can be used to form hydrophilic base coats in exemplary embodiments of the present disclosure. Methods for the preparation of photo-polyacrylamide are described in U.S. Pat. No. 6,007,833, the disclosure of which is incorporated herein by reference.

Other embodiments of hydrophilic base coats include derivatives of photo-polyacrylamide polymers incorporating additional reactive moieties. Some exemplary reactive moieties include N-oxysuccinimide and glycidyl methacrylate. Representative photo-polyacrylamide derivatives incorporating additional reactive moieties include poly(acrylamide-co-maleic-6-aminocaproic acid-N-oxysuccinimide-co-N-(3-(4-benzoylbenzamido)propyl)methacrylamide) and poly(acrylamide-co-(3-(4-benzoylbenzamido)propyl)methacrylamide)-co-glycidylmethacrylate. Additional photo-polyacrylamide polymers incorporating reactive moieties are described in U.S. Pat. No. 6,465,178 (to Chappa, et al.), U.S. Pat. No. 6,762,019 (to Swan, et al.) and U.S. Pat. No. 7,309,593 (to Ofstead, et al.), the disclosures of which are herein incorporated by reference.

Other embodiments of exemplary hydrophilic base coats that include derivatives of photo-polyacrylamide polymers incorporating additional reactive moieties can be found in U.S. Pat. No. 6,514,734 (to Clapper, et al.), the disclosure of which is incorporated herein by reference in its entirety.

In yet other embodiments, the hydrophilic base coat can include derivatives of photo-polyacrylamide polymers incorporating charged moieties. Charged moieties include both positively and negatively charged species. Exemplary charged species include, but are not limited to, sulfonates, phosphates and quaternary amine derivatives. Some examples include the negatively charged species N-acetylated poly(acrylamide-co-sodium-2-acrylamido-2-methylpropanesulfonate-co-N-(3-(4-benzoylbenzamido)propyl)methacrylamide)-co-methoxy poly(ethylene glycol) monomethacrylate. Other negatively charged species that can be incorporated into the hydrophilic base coat are described in U.S. Pat. No. 4,973,993, the disclosure of which is incorporated herein by reference in its entirety. Positively charged species can include poly(acrylamide-co-N-(3-(4-benzoylbenzamido)propyl)methacrylamide)-co-(3-(methacryloylamino)propyl)trimethylammonium chloride. Other positively charged species that can be incorporated into the hydrophilic base coat are described in U.S. Pat. No. 5,858,653 (to Duran et al.), the disclosure of which is incorporated herein by reference in its entirety.

In another embodiment, the polymers and copolymers as described are derivatized with one or more polymerizable group(s). Polymers with pendent polymerizable groups are commonly referred to as macromers. The polymerizable group(s) can be present at the terminal portions (ends) of the polymeric strand or can be present along the length of the polymer. In one embodiment polymerizable groups are located randomly along the length of the polymer.

Exemplary hydrophilic polymer coatings can be prepared using polymer grafting techniques. Polymer grafting techniques can include applying a nonpolymeric grafting agent and monomers to a substrate surface then causing polymerization of the monomers on the substrate surface upon appropriate activation (for example, but not limited to, UV radiation) of the grafting agent. Grafting methods producing hydrophilic polymeric surfaces are exemplified in U.S. Pat. Nos. 7,348,055; 7,736,689 and 8,039,524 (all to Chappa et al.) the full disclosures of which are incorporated herein by reference.

Optionally, the coating can include a crosslinking agent. A crosslinking agent can promote the association of polymers in the coating, or the bonding of polymers to the coated surface. The choice of a particular crosslinking agent can depend on the ingredients of the coating composition.

Suitable crosslinking agents can include two or more activatable groups, which can react with the polymers in the composition. Suitable activatable groups can include photoreactive groups as described herein, like aryl ketones, such as acetophenone, benzophenone, anthraquinone, anthrone, quinone, and anthrone-like heterocycles. A crosslinking agent including a photoreactive group can be referred to as a photo-crosslinker or photoactivatable crosslinking agent. The photoactivatable crosslinking agent can be ionic, and can have good solubility in an aqueous composition. Thus, in some embodiments, at least one ionic photoactivatable crosslinking agent can be used to form the coating. The ionic crosslinking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable crosslinking agents include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,077,698 (Swan et al.), U.S. Pat. No. 6,278,018 (Swan), U.S. Pat. No. 6,603,040 (Swan) and U.S. Pat. No. 7,138,541 (Swan) the disclosures of which are incorporated herein by reference.

Other exemplary ionic photoactivatable crosslinking agents include ethylenebis(4-benzoylbenzyldimethylammonium) dibromide and hexamethylenebis(4-benzoylbenzyldimethylammonium) dibromide and the like. See U.S. Pat. No. 5,714,360 (Swan et al.) the disclosures of which are incorporated herein by reference.

In yet other embodiments, restrained multifunctional reagents with photoactivable crosslinking groups can be used. In some examples these restrained multifunctional reagents include tetrakis (4-benzoylbenzyl ether) of pentaerthyritol and the tetrakis (4-benzoylbenzoate ester) of pentaerthyritol. See U.S. Pat. No. 5,414,075 (Swan et al.) and U.S. Pat. No. 5,637,460 (Swan et al.) the disclosures of which are incorporated herein by reference.

Additional crosslinking agents can include those having formula $Photo^1$-LG-$Photo^2$, wherein $Photo^1$ and $Photo^2$ independently represent at least one photoreactive group and LG represents a linking group comprising at least one silicon or at least one phosphorus atom, wherein the degradable linking agent comprises a covalent linkage between at least one photoreactive group and the linking group, wherein the covalent linkage between at least one photoreactive group and the linking group is interrupted by at least one heteroatom. See U.S. Pat. No. 8,889,760 (Kurdyumov, et al.), the disclosure of which is incorporated herein by reference. Further crosslinking agents can include those having a core molecule with one or more charged groups and one or more photoreactive groups covalently attached to the core molecule by one or more degradable linkers. See U.S. Publ. Pat. App. No. 2011/0144373 (Swan, et al.), the disclosure of which is incorporated herein by reference.

Crosslinking agents used in accordance with embodiments herein can include those with at least two photoreactive groups. Exemplary crosslinking agents are described in U.S. Pat. No. 8,889,760, the content of which is herein incorporated by reference in its entirety.

In some embodiments, the first and/or second crosslinking agent can have a molecular weight of less than about 1500 kDa. In some embodiments the crosslinking agent can have a molecular weight of less than about 1200, 1100, 1000, 900, 800, 700, 600, 500, or 400.

In some embodiments, at least one of the first and second crosslinking agents comprising a linking agent having formula Photo$^1$-LG-Photo$^2$, wherein Photo$^1$ and Photo$^2$, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In some embodiments, at least one of the first and second crosslinking agents comprising a linking agent having a formula selected from:

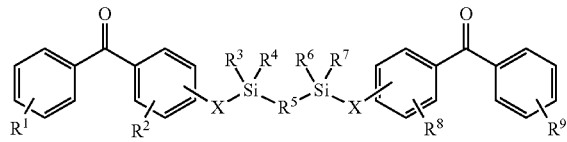

wherein R1, R2, R8 and R9 are any substitution; R3, R4, R6 and R7 are alkyl, aryl, or a combination thereof; R5 is any substitution; and each X, independently, is O, N, Se, S, or alkyl, or a combination thereof;

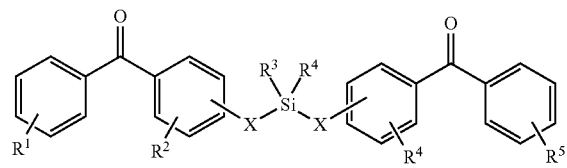

wherein R1 and R5 are any substitution; R2 and R4 can be any substitution, except OH; R3 can be alkyl, aryl, or a combination thereof; and X, independently, are O, N, Se, S, alkylene, or a combination thereof;

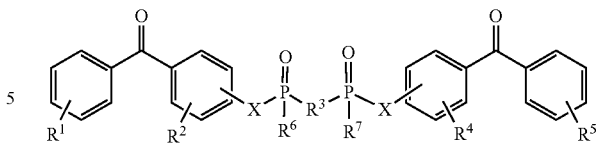

wherein R1, R2, R4 and R5 are any substitution; R3 is any substitution; R6 and R7 are alkyl, aryl, or a combination thereof; and each X can independently be 0, N, Se, S, alkylene, or a combination thereof; and

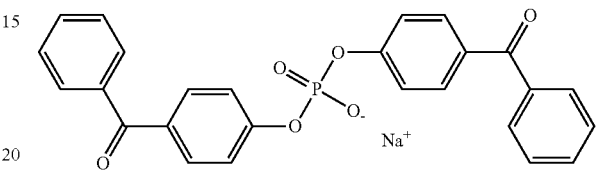

In a particular embodiment, the crosslinking agent can be bis(4-benzoylphenyl) phosphate.

In some embodiments, the photoactivatable crosslinking agent can be ionic, and can have good solubility in an aqueous composition, such as the first and/or second coating composition. Thus, in some embodiments, at least one ionic photoactivatable crosslinking agent is used to form the coating. In some cases, an ionic photoactivatable crosslinking agent can crosslink the polymers within the second coating layer which can also improve the durability of the coating.

Any suitable ionic photoactivatable crosslinking agent can be used. In some embodiments, the ionic photoactivatable crosslinking agent is a compound of formula I: $X_1$—Y—$X_2$ where Y is a radical containing at least one acidic group, basic group, or a salt of an acidic group or basic group. $X_1$ and $X_2$ are each independently a radical containing a latent photoreactive group. The photoreactive groups can be the same as those described herein. Spacers can also be part of $X_1$ or $X_2$ along with the latent photoreactive group. In some embodiments, the latent photoreactive group includes an aryl ketone or a quinone.

The radical Y in formula I provides the desired water solubility for the ionic photoactivatable crosslinking agent. The water solubility (at room temperature and optimal pH) is at least about 0.05 mg/ml. In some embodiments, the solubility is about 0.1 to about 10 mg/ml or about 1 to about 5 mg/ml.

In some embodiments of formula I, Y is a radical containing at least one acidic group or salt thereof. Such a photoactivatable crosslinking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic crosslinking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; $X_1$ and $X_2$ can contain photoreactive groups such as aryl ketones. Such compounds include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5- bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate. For example, compounds of formula I can have a Y radical that contains an ammonium group; $X_1$ and $X_2$ can contain photoreactive groups that include aryl ketones. Such photoactivatable crosslinking agents include ethylenebis(4-benzoylbenzyldimethylammonium) salt; hexamethylenebis (4-benzoylbenzyldimethylammonium) salt; 1,4-bis(4-benzoylbenzyl)-1,4-dimethylpiperazinediium) salt, bis(4-benzoylbenzyl) hexamethylenetetraminediium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium] salt; and 1,1,4,4-tetrakis (4-benzoylbenzyl)piperzinediium salt. See U.S. Pat. No. 5,714,360. The counter ion is typically a carboxylate ion or a halide. On one embodiment, the halide is bromide.

In other embodiments, the ionic photoactivatable crosslinking agent can be a compound having the formula:

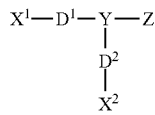

wherein $X^1$ includes a first photoreactive group; $X^2$ includes a second photoreactive group; Y includes a core molecule; Z includes at least one charged group; $D^1$ includes a first degradable linker; and $D^2$ includes a second degradable linker. Additional exemplary degradable ionic photoactivatable crosslinking agents are described in US Patent Application Publication US 2011/0144373 (Swan et al., "Water Soluble Degradable Crosslinker"), the disclosure of which is incorporated herein by reference.

In some aspects a non-ionic photoactivatable crosslinking agent can be used. In one embodiment, the non-ionic photoactivatable crosslinking agent has the formula $XR_1R_2R_3R_4$, where X is a chemical backbone, and $R_1$, $R_2$, $R_3$, and $R_4$ are radicals that include a latent photoreactive group. Exemplary non-ionic crosslinking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

In other embodiments, the non-ionic photoactivatable crosslinking agent can be represented by the formula:

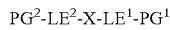

wherein $PG^1$ and $PG^2$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; $LE^1$ and $LE^2$ are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof. Other non-ionic crosslinking agents are described, for example, in U.S. application Ser. No. 13/316,030 filed Dec. 9, 2011 (Publ. No. US 2012/0149934) (Kurdyumov, "Photocrosslinker"), the disclosure of which is incorporated herein by reference.

Further embodiments of non-ionic photoactivatable crosslinking agents can include, for example, those described in US Pat. Publication 2013/0143056 (Swan et al., "Photo-Vinyl Primers/Crosslinkers"), the disclosure of which is incorporated herein by reference. Exemplary crosslinking agents can include non-ionic photoactivatable crosslinking agents having the general formula $R^1$—X—$R^2$, wherein $R^1$ is a radical comprising a vinyl group, X is a radical comprising from about one to about twenty carbon atoms, and $R^2$ is a radical comprising a photoreactive group.

A single photoactivatable crosslinking agent or any combination of photoactivatable crosslinking agents can be used in forming the coating. In some embodiments, at least one nonionic crosslinking agent such as tetrakis(4-benzoylbenzyl ether) of pentaerythritol can be used with at least one ionic crosslinking agent. For example, at least one non-ionic photoactivatable crosslinking agent can be used with at least one cationic photoactivatable crosslinking agent such as an ethylenebis(4-benzoylbenzyldimethylammonium) salt or at least one anionic photoactivatable crosslinking agent such as 4,5-bis(4-benzoyl-phenylmethyleneoxy)benzene-1,3-disulfonic acid or salt. In another example, at least one nonionic crosslinking agent can be used with at least one cationic crosslinking agent and at least one anionic crosslinking agent. In yet another example, a least one cationic crosslinking agent can be used with at least one anionic crosslinking agent but without a non-ionic crosslinking agent.

An exemplary crosslinking agent is disodium 4,5-bis[(4-benzoylbenzyl)oxy]-1,3-benzenedisulfonate (DBDS). This reagent can be prepared by combining 4,5-Dihydroxylbenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360, incorporated herein by reference).

Further crosslinking agents can include the crosslinking agents described in U.S. Publ. Pat. App. No. 2010/0274012 (to Guire et al.) and U.S. Pat. No. 7,772,393 (to Guire et al.) the content of all of which is herein incorporated by reference. In some embodiments, crosslinking agents can include boron-containing linking agents including, but not limited to, the boron-containing linking agents disclosed in US Pat. Publication 2013/0302529 entitled "Boron-Containing Linking Agents" by Kurdyumov et al., the content of which is herein incorporated by reference. By way of example, linking agents can include borate, borazine, or boronate groups and coatings and devices that incorporate such linking agents, along with related methods. In an embodiment, the linking agent includes a compound having the structure (I):

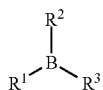 (I)

wherein $R^1$ is a radical comprising a photoreactive group; $R^2$ is selected from OH and a radical comprising a photoreactive group, an alkyl group and an aryl group; and $R^3$ is selected from OH and a radical comprising a photoreactive group. In some embodiments the bonds B—$R^1$, B—$R^2$ and B—$R^3$ can be chosen independently to be interrupted by a heteroatom, such as O, N, S, or mixtures thereof.

Additional agents for use with embodiments herein can include stilbene-based reactive compounds including, but not limited to, those disclosed in U.S. Pat. No. 8,487,137, entitled "Stilbene-Based Reactive Compounds, Polymeric Matrices Formed Therefrom, and Articles Visualizable by Fluorescence" by Kurdyumov et al., the content of which is herein incorporated by reference.

Additional photoreactive agents, crosslinking agents, hydrophilic coatings, and associated reagents are disclosed in U.S. Pat. No. 8,513,320 (to Rooijmans et al.); U.S. Pat. No. 8,809,411 (to Rooijmans); and 2010/0198168 (to Rooijmans), the content of all of which is herein incorporated by reference.

Natural polymers can also be used to form the hydrophilic base coat. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

In some instances a tie layer can be used to form the hydrophilic base layer. In yet other instances the tie layer can be added to the hydrophilic base layer. The tie layer can act to increase the adhesion of the hydrophilic base layer to the substrate. In other embodiments, the tie layer can act to increase adhesion of the hydrophobic active agent to the hydrophilic base layer. Exemplary ties layers include, but are not limited to silane, butadiene, polyurethane and parylene. Silane tie layers are described in US Patent Publication 2012/0148852 (to Jelle, et al.), the content of which is herein incorporated by reference.

In exemplary embodiments, the hydrophilic base layer can include tannic acid, polydopamine or other catechol containing materials.

Substrates

The substrate can be formed from any desirable material, or combination of materials, suitable for use within the body. In some embodiments the substrate is formed from compliant and flexible materials, such as elastomers (polymers with elastic properties). Exemplary elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, polyether-polyamide copolymers, and the like. The substrate can be made of a single elastomeric material, or a combination of materials.

Other materials for the substrate can include those formed of polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

Beyond polymers, and depending on the type of device, the substrate can also be formed of other inorganic materials such as metals (including metal foils and metal alloys), glass and ceramics.

Processes to modify substrates described above can include chemical modifications to improve performance characteristics of the substrate. Specific chemical processes that can be used include ozone treatment, chemical oxidation, acid chemical etching, base chemical etching, plasma treatment and corona treatment, surface grafting, thermally activated coating processes (both covalent and non-covalent) and surface modifications including coatings containing dopamine, tannic acid, plant polyphenols and other catechols or catechol containing derivatives of hydrophilic moieties. Additionally, processes to form substrates described above can include physical modifications for example, but not limited to, sand blasting and surface texturing (for example either during or after the molding process of polymers).

In some embodiments, the modification of substrates as described herein can allow for omission of a base coating layer (such as a hydrophilic layer) as substrate surfaces that have been modified will allow for improved adhesion of a hydrophobic therapeutic agent and cationic agent compared with that of a hydrophilic layer.

Devices

It will be appreciated that embodiments herein include, and can be used in conjunction with, various types of devices including, but not limited to, drug delivery devices such as drug eluting balloon catheters, drug-containing balloon catheters, stents, grafts, and the like.

Some embodiments described herein can be used in conjunction with balloon expandable flow diverters, and self-expanding flow diverters. Other embodiments can include uses in contact with angioplasty balloons (for example, but not limited to, percutaneous transluminal coronary angioplasty and percutaneous transluminal angioplasty). Yet other embodiments can include uses in conjunction with sinoplasty balloons for ENT treatments, urethral balloons and urethral stents for urological treatments and gastro-intestinal treatments (for example, devices used for colonoscopy). Hydrophobic active agent can be transferred to tissue from a balloon-like inflatable device or from a patch-like device. Other embodiments of the present disclosure can further be used in conjunction with micro-infusion catheter devices. In some embodiments, micro-infusion catheter devices can be used to target active agents to the renal sympathetic nerves to treat, for example, hypertension.

Embodiments included herein can also be used in conjunction with the application of various active agents to the skin (for example, but not limited to transdermal drug delivery).

Other exemplary medical applications wherein embodiments of the present disclosure can be used further encompass treatments for bladder neck stenosis (e.g. subsequent to transurethral resection of the prostrate), laryngotrachial stenosis (e.g. in conjunction with serial endoscopic dilatation to treat subglottic stenosis, treatment of oral cancers and cold sores and bile duct stenosis (e.g. subsequent to pancreatic, hepatocellular of bile duct cancer). By way of further example, embodiments herein can be used in conjunction with drug applicators. Drug applicators can include those for use with various procedures, including surgical procedures, wherein active agents need to be applied to specific tissue locations. Examples can include, but are not limited to, drug applicators that can be used in orthopedic surgery in order to apply active agents to specific surfaces of bone, cartilage, ligaments, or other tissue through physical contact of the drug applicator with those tissues. Drug applicators can include, without limitation, hand-held drug applicators, drug patches, drug stamps, drug application disks, and the like.

In some embodiments, drug applicators can include a surface having a hydrophilic polymer layer disposed thereon and coated therapeutic agent particles disposed on the hydrophilic polymer layer, the coated therapeutic agent particles comprising a particulate hydrophobic therapeutic agent; and a cationic agent disposed over the particulate hydrophobic therapeutic agent.

In use, various embodiments included herein can enable rapid transfer of therapeutic agents to specific targeted tissues. For example, in some embodiments, a care provider can create physical contact between a portion of a drug delivery device including a therapeutic agent and the tissue being targeted and the therapeutic agent will be rapidly transferred from the drug delivery device to that tissue. As such, precise control over which tissues the therapeutic agent is provided to can be achieved.

One beneficial aspect of various embodiments described herein is that the therapeutic agent can be transferred from the drug delivery device or coating to the targeted tissue very rapidly. In some embodiments substantial transfer of the therapeutic agent from the drug delivery device or coating to the tissue occurs in 30 minutes or less. In some embodiments substantial transfer of the therapeutic agent from the drug delivery device or coating to the tissue occurs in 15 minutes or less. In some embodiments substantial transfer of the therapeutic agent from the drug delivery device or coating to the tissue occurs in 10 minutes or less. In some embodiments substantial transfer of the therapeutic agent from the drug delivery device or coating to the tissue occurs in 5 minutes or less. In some embodiments substantial transfer of the therapeutic agent from the drug delivery device or coating to the tissue occurs in 2 minutes or less. In some embodiments substantial transfer of the therapeutic agent from the drug delivery device or coating to the tissue occurs in 1 minute or less.

Additional Embodiments

As described above, some embodiments can include a hydrophilic base coat or layer. In some embodiments, a hydrophilic polymer solution is formed by combining a hydrophilic polymer with one or more solvents. Exemplary hydrophilic polymers are described in greater detail above. The hydrophilic polymer solution can then be applied to a suitable substrate, such as an expandable balloon disposed on a catheter shaft. Many different techniques can be used to apply the hydrophilic polymer solution to the substrate. By way of example, exemplary techniques can include brush coating, drop coating, blade coating, dip coating, spray coating, micro-dispersion, and the like.

In some embodiments, such as where a photo-polymer is used to form the hydrophilic layer, an actinic radiation application step can be performed in order to activate latent photoreactive groups on the hydrophilic polymer or on a crosslinker in order to covalently bond the hydrophilic polymer the substrate surface. By way of example, after applying the hydrophilic polymer solution to the substrate, the device can be subjected to UV exposure at a desirable wavelength for a period of time. Next a hydrophobic active agent can be obtained and processed in order to prepare it for deposition. In some embodiments, processing of the hydrophobic active agent can include steps such as milling of the active agent. In some embodiments, processing of the hydrophobic active agent can include steps such as recrystallization of the active agent. In some embodiments, processing of the hydrophobic active agent can include lyophilizing of the active agent.

In various embodiments, the hydrophobic active agent, as a particulate, can be suspended in water. Using the hydrophobic active agent and a cationic agent, coated therapeutic agent particles can be formed. By way of example, a cationic agent, in water or a different solvent, can be added to the hydrophobic active agent suspension. In various embodiments, a mixing or agitation step can be performed in order to allow the hydrophobic active agent to interface with the cationic agent. In some embodiments, the cationic agent will surround the particulate hydrophobic active agent.

In some embodiments, a nucleic acid solution can be added to the mixture, either before or after addition of the cationic agent and the mixing/agitation steps. In some embodiments, an additive component such as those described above can be added to the mixture. The mixture can be applied to the substrate of a device, either directly or on top of a hydrophilic base coat. By way of example, exemplary techniques for application can include brush coating, drop coating, blade coating, dip coating, spray coating, micro-dispersion and the like After application, the composition can be allowed to dry. In the context of drug eluting balloon catheters or a drug-containing balloon catheter, for example, the balloons can be folded, pleated and sheathed in a sheath. In some embodiments, balloons can be placed in an oven for a period of time.

In some embodiments of the present disclosure, an active agent that is not hydrophobic can be modified to be essentially hydrophobic for disposition on the hydrophilic polymer layer. Exemplary modifications can include the preparation of prodrugs, whereby the hydrophobicity of the active agent can be modified by covalent linkage to a polymer. Other exemplary prodrugs can include an active agent that is formed in-situ by bond cleavage of the prodrug. Other exemplary modifications can include, but are not limited to, particles (e.g. nanoparticles or microparticles) containing the active agent encapsulated in a hydrophobic polymer. In some embodiments the hydrophobic polymer can be biodegradable, releasing the active agent upon delivery to the targeted tissue. Other exemplary modifications can include, but are not limited to, micelles or other constructs of the like with altered hydrophobicity, formed as a result of the interaction between the active agent and a lipid additive.

Microparticle preparations of the present disclosure can include additional excipients to modify the surface of the microparticle for a particular application. For example, surface modifications to the microparticle resulting in a microparticle with a positive or negative zeta-potential may be advantageous. Exemplary materials that can be used to modify the zeta-potential of the surface of the microparticle include, but are not limited to polyacrylic acid (PAA), polyglutamic acid, polyaspartic acid, heparin, alginate, hyaluronic acid and polyvinylsulfonic acid. Cationic polymers described above can also be exemplary materials used to modify the zeta-potential of the surface of the microparticle.

The present invention may be better understood with reference to the following examples. These examples are intended to be representative of specific embodiments of the invention, and are not intended as limiting the scope of the invention.

EXAMPLES

Example 1:

Paclitaxel Preparation and Balloon Coating Procedure

"Jar-Milled Paclitaxel": Paclitaxel (LC laboratories) was suspended in water at 65 mg/mL and milled using 5 mm stabilized zirconia 5×5 mm cylindrical beads (Stanford Materials Corp). After milling for 18 hours the slurry was removed from the beads and lyophilized.

"Sonicated Paclitaxel": Paclitaxel crystals were obtained by suspending paclitaxel (LC Laboratories) in water at 50 mg/mL. The paclitaxel was micronized using a sonic probe for 30 seconds, and leaving the resulting suspension for three days at room temperature on an orbital shaker with a 1 hour sonication treatment per day in a sonic bath over the course of the three days. The mixture was lyophilized.

Unless otherwise indicated the following NYLON balloons were used in all studies: 20×3.5 mm.

Hydrophilic basecoats (R) were deposited onto the nylon balloon surfaces. The hydrophilic basecoat solution included 6.25 g/L polyvinyl pyrrolidone (PVP) with benzoylbenzoic acid groups; 1.25 g/L polyacrylamide; 2.5 g/L PVP (K90); and 0.05 g/L photo-crosslinker; in a solvent solution of 85:15 water/isopropanol. For examples 1-15, crosslinkers were prepared as described in U.S. Pat. No. 6,278,018, Swan. For examples 16-24, crosslinkers were prepared as described in US Patent Application Publication 2012/0046384, Kurdyumov et al. and U.S. Pat. No. 6,278,018, Swan. After coating the basecoat material was dried at room temperature for 15 minutes and then irradiated with UV light for 3 minutes.

Typically, for any given formulation, an amount of 3 μg/mm$^2$ paclitaxel for coating on the balloons was attempted (which is 660 μg paclitaxel per balloon). The paclitaxel containing coating mixture was applied on top of the cured hydrophilic basecoat (R) by means of a positive displacement pipette and dried using a hot air-gun.

All balloons were dried over night at room temperature. The balloons were folded, pleated and sheathed in a nylon sheath. The balloons were subsequently placed in a 55° C. oven for 1 hour.

Chemicals were obtained from Sigma Aldrich unless stated otherwise. Amounts (μg) of active agent transferred to the tissue and standard deviations for Examples 2-15 are listed in Table 3. Amounts (μg) of active agent transferred to the tissue and standard deviations for Examples 16-24 are listed in Table 9.

Example 2:

Formulations with DOTAP and siRNA

Jar milled lyophilized paclitaxel was suspended in water at 67 mg/mL. To 100 μL suspension 31 μL DOTAP at 20 mg/mL in ethanol (Avanti Polar Lipids) was added and sonicated for 10 minutes in a sonic bath. Then 4.4 μL of 1 mM non-coding siRNA, 0.065 mg, was added. Three balloons received a hydrophilic basecoat (R) and a paclitaxel containing topcoat according to the procedure as described in Example 1. 8 μL of the paclitaxel containing mixture was used for the topcoat.

To 130 μL of the paclitaxel/DOTAP/siRNA containing mixture 3.7 mg glycogen (available from VWR) was added (74 μL of a 50 mg/mL solution in water). Four balloons received a hydrophilic basecoat (R) and a paclitaxel containing topcoat with glycogen according to the procedure as described in Example 1. The paclitaxel-containing mixture (8 μL) was used for the topcoat.

All balloons were dried over night at room temperature. The balloons were folded, pleated and sheathed in a nylon sheath. The balloons were subsequently placed in a 55° C. oven for 1 hour.

Release of the paclitaxel from the coating was then assessed according to the following procedure. Excised pig coronary arteries (Pel-Freez Biologicals) were prepared and kept at 37° C. Upon removal of the sheaths from the balloons, the balloons were soaked in PBS at 37° C. for 30 seconds and then removed from the PBS. Next, the balloon was expanded in the artery tissue at 60-80 psi for 30 seconds at 37° C. and after deflation and removal of the balloon, the artery tissue was rinsed with PBS at 37° C. After removal of the balloon from the tissue and rinsing, the tissue was placed in a methanol/0.1% acetic acid solution. The resulting methanol and acetic acid solution was tested for paclitaxel content using HPLC ("Drug Transfer to Tissue").

Example 3:

Formulations with DOTAP and siRNA

Formulation 1—"PAX+DOTAP1x"

Jar milled paclitaxel was suspended in water at 65 mg/mL and treated with a sonic probe for 30 seconds. 100 mg of the suspension (6.35 mg paclitaxel) was weighed out and 32 μL DOTAP 20 mg/mL solution in ethanol was added. The mixture was sonicated for 10 minutes. The balloon received a hydrophilic basecoat (R) and a paclitaxel containing topcoat according to the procedure as described in Example 1. The paclitaxel-containing mixture (10 μL) was used for the topcoat.

Formulation 2—"PAX+DOTAP2x"

Jar milled paclitaxel was suspended in water at 65 mg/mL and treated with sonic probe for 30 seconds. 100 mg of the suspension (6.35 mg paclitaxel) was weighed out and 64 μL DOTAP 20 mg/mL solution in ethanol was added. The mixture was sonicated for 10 minutes. The balloon received a hydrophilic basecoat (R) and a paclitaxel containing topcoat according to the procedure as described in Example 1. The paclitaxel-containing mixture (10 μL) was used for the topcoat.

Formulation 3—"PAX+DOTAP1x+si"

To formulation 1, 60 μg siRNA was added (4.2 μL 1 mM solution). The balloon received a hydrophilic basecoat (R) and a paclitaxel containing topcoat according to the procedure as described in Example 1. The paclitaxel-containing mixture (10 μL) was used for the topcoat.

Formulation 4—"PAX+DOTAP2x+si"

To formulation 2, 120 μg siRNA was added: 8.4 μL 1 mM solution. The balloon received a hydrophilic basecoat (R) and a paclitaxel containing topcoat according to the procedure as described in Example 1. The paclitaxel-containing mixture (10 μL) was used for the topcoat.

Formulation 5—"PAX+DOTAP1x+si+F68"

To formulation 3, 4 μL F68 @ 100 mg/mL in water was added (400 μg, ~6% w/w total formulation). The balloon received a hydrophilic basecoat (R) and a paclitaxel containing topcoat according to the procedure as described in Example 1. The paclitaxel containing mixture (10 μL) was used for the topcoat.

Formulation 6—"PAX+DOTAP2x+si+F68"

To formulation 4, 4 μL F68 @ 100 mg/mL in water was added (400 μg, ~6% w/w total formulation). The balloon received a hydrophilic basecoat (R) and a paclitaxel containing topcoat according to the procedure as described in Example 1. The paclitaxel containing mixture (10 μL) was used for the topcoat.

All balloons were dried over night at room temperature. The balloons were folded, pleated and sheathed in a nylon sheath. The balloons were subsequently placed in a 55° C. oven for 1 hour.

Release of the paclitaxel from the coating was then assessed according to the procedure as described in example 2.

Example 4:

Formulations with DOTAP

Jar-milled paclitaxel (as above) was used. Alternatively, paclitaxel was micronized using a Netsch micronizer, and freeze dried.

Paclitaxel Netsch milled particles were suspended at 67 mg/mL in water and sonicated for 10 minutes.

Paclitaxel jar milled particles were suspended at 67 mg/mL in water and sonicated for 10 minutes.

Formulation 1

100 mg of the suspension of Netsch milled paclitaxel @ 67 mg/mL in DDW (6.28 mg paclitaxel) was weighed out and sonicated until well dispersed. DOTAP 20 mg/mL solution in ethanol (31.4 μL) was added and sonicated in sonic bath for 10 minutes. Two balloons each received a hydrophilic basecoat (R) and a paclitaxel containing topcoat according to the procedure as described in Example 1. The paclitaxel-containing mixture (14 μL) was used for the topcoat.

Formulation 2

100 mg of the suspension of Netsch milled paclitaxel @ 67 mg/mL in DDW (6.28 mg paclitaxel) was weighed out and sonicated until well dispersed. 0.628 mg DOTAP (31.4 μL DOTAP 20 mg/mL in ethanol) was added and sonicated in sonic bath for 10 minutes. Then 0.063 mg siRNA: 4.4 μL siRNA @ 1 mM, 14.2 mg/ml was added and vortexed well; sonicated for 5 minutes. 4 μL F68 at 10 mg/ml in water was added. Two balloons each received a hydrophilic basecoat (R) and a paclitaxel containing topcoat according to the procedure as described in Example 1. The paclitaxel containing mixture (15 μL) was used for the topcoat.

Formulation 3

100 mg of the suspension of jar milled paclitaxel @ 67 mg/mL in DDW (6.28 mg paclitaxel) was weighed out and sonicated until well dispersed. 31.4 μL DOTAP 20 mg/mL solution in ethanol was added and sonicated in sonic bath for 10 minutes. Two balloons each received a hydrophilic basecoat (R) and a paclitaxel containing topcoat according to the procedure as described in Example 1. The paclitaxel-containing mixture (14 μL) was used for the topcoat. Only one balloon was tested.

Formulation 4

200 mg of the suspension of jar milled paclitaxel @ 67 mg/mL in DDW (12.56 mg paclitaxel) was weighed out and sonicated until well dispersed. 2.51 mg DOTAP (126 μL DOTAP 20 mg/mL in ethanol) was added and sonicated in sonic bath for 10 minutes. Two balloons each received a hydrophilic basecoat (R) and a paclitaxel containing topcoat according to the procedure as described in Example 1. The paclitaxel containing mixture (17.5 μL) was used for the topcoat.

Formulation 5

100 mg of the suspension of jar milled paclitaxel @ 67 mg/mL in DDW (6.28 mg paclitaxel) was weighed out and sonicated until well dispersed. 0.628 mg DOTAP (31.4 μL DOTAP 20 mg/mL in ethanol) was added and sonicated in sonic bath for 10 minutes. 4 μL F68 at 10 mg/ml in water was added (0.6% vs paclitaxel, or total). Two balloons each received a hydrophilic basecoat (R) and a paclitaxel containing topcoat according to the procedure as described in Example 1. The paclitaxel containing mixture (15 μL) was used for the topcoat.

Formulation 6

130 μL of formulation 4 was transferred to a new tube and added 4 μL F68 at 100 mg/mL in water (0.5%). Two balloons received a hydrophilic basecoat (R) and a paclitaxel containing topcoat according to the procedure as described in Example 1. The paclitaxel-containing mixture (17.5 μL) was used for the topcoat.

Formulation 7

200 mg of the suspension of jar milled paclitaxel at 67 mg/mL in DDW (12.56 mg paclitaxel) was weighed out and sonicated until well dispersed. 1.26 mg DOTAP: 63 μL DOTAP 20 mg/mL in ethanol was added and sonicated in sonic bath for 10 minutes. Then 0.126 mg siRNA: 8.8 μL siRNA at 1 mM, 14.2 mg/ml was added and vortexed well; sonicated for 5 minutes. 8 μL F68 at 10 mg/ml in water was added. Two balloons each received a hydrophilic basecoat (R) and a paclitaxel containing topcoat according to the procedure as described in Example 1. of the paclitaxel containing mixture (15 μL) was used for the topcoat.

All balloons were dried over night at room temperature. The balloons were folded, pleated and sheathed in a nylon sheath. The balloons were subsequently placed in a 55° C. oven for 1 hour. Release of the paclitaxel from the coating was then assessed according to the procedure as described in example 2.

Example 5:

Coating Transfer from Rods

The top surface of 5 cm long rods having a 5 mm diameter were coated with the hydrophilic base coat (R) as described above. The coating was applied by brushing the surfaces of the rods with the solution, drying for 15 minutes at room temperature and subsequently irradiating for 3 minutes with UV. Three formulations were prepared:

Formulation 1

Jar-milled paclitaxel was suspended in water at 67 mg/mL. 100 mg of the suspension (6.28 mg paclitaxel) was weighed out and sonicated until well dispersed. 1.26 mg DOTAP (62.8 μL DOTAP 20 mg/mL in ethanol) was added and sonicated in sonic bath for 10 minutes.

Formulation 2

Jar-milled paclitaxel was suspended in water at 67 mg/mL. 100 mg of the suspension (6.28 mg paclitaxel) was weighed out and sonicated until well dispersed. 1.26 mg DOTAP (62.8 μL DOTAP 20 mg/mL in ethanol) was added and sonicated in sonic bath for 10 minutes. Then F68 was added 5% w/w total formulation as a 100 mg/mL solution in water Formulation 3

Jar-milled paclitaxel was suspended in water at 67 mg/mL. 100 mg of the suspension (6.28 mg paclitaxel) was weighed out and sonicated until well dispersed. 1.26 mg DOTAP (62.8 μL DOTAP 20 mg/mL in ethanol) was added and sonicated in sonic bath for 10 minutes. Then 62.8 μL dextran (100 mg/mL in water) was added.

In triplicate, the rods received the paclitaxel containing topcoat by pipetting 5 μL of one of the formulations and letting dry at room temperature overnight.

Ex vivo pig skin tissue was trimmed from fat and excised with a 8 mm tissue excision tool (Sklar) and kept at 37° C. The rods were soaked for 30 seconds in PBS at 37° C. Subsequently the rods were impressed into the excised tissue for 30 seconds. The tissue samples were placed in a methanol/0.1% acetic acid solution in a vial with tissue disruption media. The tissue was disrupted to extract transferred paclitaxel Example 6:

Varying Ratios of Components

10 NYLON balloon stubs received a hydrophilic basecoat (R) according to the procedure as described in Example 1.

Jar-milled paclitaxel was suspended in water at 65 mg/mL. DOTAP dissolved in ethanol at 25 mg/mL was added to the formulation at 20 or 40% w/w paclitaxel and sonicated in sonic bath for 10 minutes. To some of the resulting mixtures gelatine B, glycogen or dextran was added as a 100 mg/mL solution in water at 33% or 50% w/w total matrix. The formulations were applied as a topcoat on the balloon (following the procedure in Example 1), aiming for approximately for a total of 700 μg paclitaxel in the coating. The balloons were folded, pleated and sheathed in a nylon sheath. The balloons were subsequently placed in a 55° C. oven for 1 hour.

Release of the paclitaxel from the coating was then assessed according to the procedure as described in example 2.

Example 7:

Formulations with PLURONIC® F68

Formulations were prepared by suspending jar-milled paclitaxel in water at 65 mg/mL. DOTAP dissolved in ethanol at 25 mg/mL was added to the formulation at 20% w/w paclitaxel. To the resulting mixtures PLURONIC® F68 (BASF Corporation) was added as a 10 or 100 mg/mL solution in water, reaching 0.6-5% w/w of the total matrix. The formulations were top-coated on balloons with hydrophilic base-coats R as described in experiment 1.

All balloons were dried over night at room temperature. The balloons were folded, pleated and sheathed in a nylon sheath. The balloons were subsequently placed in a 55° C. oven for 1 hour.

Release of the paclitaxel from the coating was then assessed according to the procedure as described in example 2.

Example 8:

Amorphous Paclitaxel Nanoparticles with DOTAP or Polyethyleneimine (i) Preparation of amorphous paclitaxel particles:
In triplicate, an average of 6.2 mg of paclitaxel was dissolved in 50 μL chloroform. The solution was dispersed in 1 mL BSA at 50 mg/mL in water using a sonic probe for 20 seconds. The obtained emulsions were spun in a centrifuge for 15 minutes at 5000 rpm. The clear supernatant was aspirated; the residue was frozen and lyophilized. The residues weighed on average 9.8 mg. To remove the remaining BSA, the solids were dispersed in 1 mL of fresh water using a sonic bath and subsequently spun for 10 minutes at 10,000 rpm. The supernatant was aspirated.

(ii) Preparation of DOTAP dispersion in water:
5 mL of a DOTAP solution at 25 mg/mL in ethanol was placed in a glass round-bottom container and evaporated under vacuum to obtain a film. The DOTAP was dispersed in 12.5 mL water by adding batches of 4.2 mL water to the glass container and briefly sonication in a sonic bath. The batches were combined, sonicated for 10 minutes in a sonic bath and filtered through a 0.45 μm filter.

Balloons were base- and top-coated following the procedure described in Example 1. In order to obtain the formulations for the paclitaxel containing topcoats, DOTAP dispersed in water or an aqueous solution of PEI was added to the obtained amorphous paclitaxel particles as follows:

1. 114 μL of a DOTAP dispersion in water at 10 mg/mL was added to 5.7 μg paclitaxel. 15 μL was used to coat balloon material,
2. 62 μL polyethyleneimine low molecular weight (PEI-LMW) at 20 mg/mL with 31 μL water was added to 6.2 μg paclitaxel. 10 μL was used to coat balloon material,
3. 67 μL polyethyleneimine 750 kDa (PEI-HMW) at 20 mg/mL with 33 μL water was added to 6.7 μg paclitaxel. 10 μL was used to coat balloon material.

All balloons were dried over night at room temperature. The balloons were folded, pleated and sheathed in a nylon sheath. The balloons were subsequently placed in a 55° C. oven for 1 hour.

Release of the paclitaxel from the coating was then assessed according to the procedure as described in example 2.

Example 9:

Z-Potential Measurements

Paclitaxel (5 mg) was dissolved in 10 μL benzyl alcohol. The solution was dispersed in 1 mL BSA at 50 mg/mL in water using a sonic probe for 20 seconds. The obtained emulsion was divided into 5 times 200 μL portions which were spun in a centrifuge for 10 minutes at 10000 rpm (residuals A-E). The clear supernatant was aspirated.

A. The residue was resuspended in 1 mL of DDW. This mixture was diluted 10 times.

B. 10 μL of a chitosan solution 10 mg/mL in 1% acetic acid was added with 10 μL DDW. The resulting suspension was diluted in DDW 10 times.

C. 1 mL of a protamine solution 1 mg/mL in DDW was added. The resulting suspension was diluted in DDW 10 times.

D. The solids were dispersed in 500 μL of DDW using a sonic bath and subsequently spun for 10 minutes at 10,000 rpm. The supernatant was aspirated. 5 mL of a DOTAP solution at 25 mg/mL in ethanol was placed in a glass round-bottom container and evaporated under vacuum to obtain a film. The DOTAP was dispersed in 12.5 mL water by adding batches of 4.2 mL water to the glass container and briefly sonication in a sonic bath. The batches were combined, sonicated for 10 minutes in a sonic bath and filtered through a 0.45 µm filter. To the amorphous paclitaxel residue 25 µL of a DOTAP dispersion in water at 10 mg/mL was added and sonicated in sonic bath. The resulting dispersion was diluted in DDW 10 times.

Z-sizing measurements were taken using a Z-sizer (available from Malvern) showing the formation of negatively charged droplets upon dispersion of dissolved PTX in a BSA solution. Positively charged particles were obtained upon addition of chitosan, protamine or DOTAP solutions.

TABLE 2

Temperature (° C.) and ZP values (mV) for Example 9.

| Sample Name | T (° C.) | ZP (mV) |
| --- | --- | --- |
| PTX/BSA in Water | 25 | −23.1 |
| Chitosan | 25 | +63.8 |
| DOTAP | 25 | +58 |
| Protamine | 37 | +12.3 |

Example 10:

F68 on PTX/DOTAP Formulation

Formulations were prepared by suspending jar-milled paclitaxel in water at 65 mg/mL. DOTAP dissolved in ethanol at 25 mg/mL was added to the formulation at 20% w/w paclitaxel. To the resulting mixtures F68 was added 2-16 µL at 100 mg/mL solution in water, reaching 5-34% w/w of the total matrix (50% w/w PTX). The balloon stubs were base- and top-coated following the procedure described in example 1. Additionally a PTX/DOTAP 80:20% w/w formulation was tested. The formulations were top-coated on balloon stubs with hydrophilic base-coat F (n=2 per formulation).

The balloons were folded, pleated and sheathed in a nylon sheath. The balloons were subsequently placed in a 55° C. oven for 1 hour.

Release of the paclitaxel from the coating was then assessed according to the procedure as described in example 2.

Example 11:

Use of Amorphous PTX and Different Cationic Moieties

Four balloons were base- and top-coated following the procedure described in experiment 1. The following formulations were top-coated on balloon-stubs with hydrophilic base-coat R. (n=1 per formulation).

In each of 4 tubes 5-7 mg of paclitaxel was dissolved in 50 µL chloroform. The solution was dispersed in 1 mL BSA at 50 mg/mL in water using a sonic probe for 20 seconds. The obtained emulsions were spun in a centrifuge for 10 minutes at 5000 rpm. The clear supernatant was aspirated and the residue was frozen on dry ice and subsequently lyophilized. ("paclitaxel residue").

A. Started with 4.8 µg paclitaxel. Paclitaxel residue was reconstituted in 96 µL DDW. 14 µL was used to coat balloon material.

B. Started with 7.1 µg paclitaxel. Residual BSA was removed by dispersing the solids in 1 mL of fresh water using a sonic bath and subsequently spun for 10 minutes at 10,000 rpm. The supernatant was aspirated. 5 mL of a DOTAP solution at 25 mg/mL in ethanol was placed in a glass round-bottom container and evaporated under vacuum to obtain a film. The DOTAP was dispersed in 12.5 mL water by adding batches of 4.2 mL water to the glass container and briefly sonication in a sonic bath. The batches were combined, sonicated for 10 minutes in a sonic bath and filtered through a 0.45 µm filter. 142 µL of the DOTAP dispersion in water at 10 mg/mL was added to the paclitaxel residue. 14 µL was used to coat balloon material.

C. Started with 7.1 µg paclitaxel. Chitosan was dissolved in 1% acetic acid at 100 mg/mL and 57 µL was added to the paclitaxel residue. Then 57 µL DDW was added. Particles were dispersed using a sonic bath. The balloon was coated with 14 µL of this material.

D. Started with 5.1 µg paclitaxel. Protamine was dissolved in DDW at 10 mg/mL. 51 µL of the protamine solution was added with additional 51 µL DDW to the paclitaxel residue. Particles were dispersed using a sonic bath. The balloon was coated with 14 µL of this material.

The balloons were folded, pleated and sheathed in a nylon sheath. The balloons were subsequently placed in a 55° C. oven for 1 hour.

Release of the paclitaxel from the coating was then assessed according to the procedure as described in example 2

Example 12:

Study IV Flow Experiment

Full length balloon catheters received hydrophilic base coats as described in experiment 1. Paclitaxel containing formulations were coated on full length catheter balloons and tested in ex-vivo pig coronary arteries in the flow experiment.

1.) Flow systems: Two open flow loops of PBS in the system were used. One, circulating at 70 mL/min, 2 L total and at 37° C. was for the artery in which the balloon is tested. The other, at 280 mL/min, 1 L total and at 37° C., was for a manifold that supported four arteries at once (flow at the output was thus 70 mL/min).

2.) Artery connections: Pig coronary arteries for testing were prepared by trimming and gluing (with a cyanoacrylate gel glue ("super glue")) onto a 200 µL pipette tip. The tip was trimmed on the short end such that the opening in the tip was ~2-3 mm in diameter. After gluing, arteries were trimmed to be 30 mm from the end of the pipette tip to the free end of the artery. Arteries were held in PBS at room temperature prior to testing.

Each piece of tubing terminated in a 1 mL pipette tip that served as a means to affix arteries. At the test site, the tip was trimmed to fit into the tubing at the large end and to be larger than the diameter of the 7F guide catheter at the small end. In the manifold, the tips were trimmed to fit snugly on the Y-connectors on the large end but were not trimmed on the small end. The resistance provided by the small tip orifice ensured equal flow through the four ports.

For testing, arteries were put onto the end of the flow tubing by press-fitting the smaller yellow pipette tip onto the larger blue tip.

10 mL PBS was drawn into the syringe (on hemostat Y connector) and flushed through the guide catheter to ensure the catheter was filled with PBS. The prepared pig coronary artery was placed on the test loop by pressing it onto the pipette end. Then coated balloon catheter was introduced as the hemostat was opened wide. The catheter was pushed to the point where the guide exited the catheter and the guidewire was removed. The hemostat was closed somewhat to reduce backflow. Then the balloon catheter was pushed to the treatment site inside the prepared coronary artery and the hemostat was closed tightly. The balloon was inflated to 6 ATM and held for 30 seconds. The hemostat was opened and the balloon catheter was deflated and removed. The artery was then removed from test loop and placed on second flow manifold (one of four spaces) and left for on flow manifold for 13 minutes, counted from time of deflation of the balloon. The artery was cut from pipette tip placed in a methanol/0.1% acetic acid solution. The resulting methanol and acetic acid solution was tested for paclitaxel content using HPLC ("Drug Transfer to Tissue").

Example 13:

Release of Paclitaxel from Full Length Balloon Catheters

One full length balloon catheter and 2 balloon stubs received a hydrophilic basecoat (R) according to example 1 and were coated with the following formulations:

A) Jar-milled paclitaxel was suspended in water at 67 mg/mL. 100 mg of the suspension (6.28 mg paclitaxel) was weighed out and sonicated until well dispersed. 1.26 mg DOTAP (62.8 µL DOTAP 20 mg/mL in ethanol) was added and sonicated in sonic bath for 10 minutes. Then 62.8 µL dextran (100 mg/mL in water) was added. The balloon was coated with 22.5 µL of this material.

B) Jar-milled paclitaxel was suspended in water at 67 mg/mL. 100 mg of the suspension (6.28 mg paclitaxel) was weighed out and sonicated until well dispersed. 1.26 mg DOTAP (62.8 µL DOTAP 20 mg/mL in ethanol) was added and sonicated in sonic bath for 10 minutes. Then 62.8 µL glycogen (100 mg/mL in water) was added. The balloon was coated with 22.5 µL of this material.

C) Jar-milled paclitaxel was suspended in water at 67 mg/mL. 100 mg of the suspension (6.28 mg paclitaxel) was weighed out and sonicated until well dispersed. 1.26 mg DOTAP (62.8 µL DOTAP 20 mg/mL in ethanol) was added and sonicated in sonic bath for 10 minutes. A solution of gelatin type A (100 mg/mL in water) was warmed to 37° C. Then 62.8 µL was added to the mixture. The balloon was coated with 22.5 µL of this material.

D) Jar-milled paclitaxel was suspended in water at 67 mg/mL. The suspension (100 mg; 6.28 mg paclitaxel) was weighed out and sonicated until well dispersed. A mixture of 953 µg DOTAP and 318 µg cholesterol in 51 µL ethanol was added and sonicated in sonic bath for 10 minutes. The balloon was coated with 15.5 µL of this material.

The topcoats were dried under hot air and left further to dry over night at room temperature. The balloons were then folded, pleated and sheathed in a nylon sheath. The balloons were subsequently placed in a 55° C. oven for 1 hour.

The full length catheter was tested according to the procedure in example 12.

Release of the paclitaxel from the coating on the two balloon stubs was assessed according to the procedure as described in example 2.

Example 14:

Release of Paclitaxel from Balloons

Three full-length balloon catheters per formulation received a hydrophilic basecoat (R) according to example 1 and were top-coated with the following formulations:

A) Jar-milled paclitaxel was suspended in water at 67 mg/mL. 100 mg of the suspension (6.28 mg paclitaxel) was weighed out and sonicated until well dispersed. 1.26 mg DOTAP (62.8 µL DOTAP 20 mg/mL in ethanol) was added and sonicated in sonic bath for 10 minutes. Then 62.8 µL dextran (100 mg/mL in water) was added. The balloon was coated with 22.5 µL of this material.

B) Jar-milled paclitaxel was suspended in water at 67 mg/mL. 100 mg of the suspension (6.28 mg paclitaxel) was weighed out and sonicated until well dispersed. 1.26 mg DOTAP (62.8 µL DOTAP 20 mg/mL in ethanol) was added and sonicated in sonic bath for 10 minutes. Then 62.8 µL glycogen (100 mg/mL in water) was added. The balloon was coated with 22.5 µL of this material.

C) Jar-milled paclitaxel was suspended in water at 67 mg/mL. 100 mg of the suspension (6.28 mg paclitaxel) was weighed out and sonicated until well dispersed. 1.26 mg DOTAP (62.8 µL DOTAP 20 mg/mL in ethanol) was added and sonicated in sonic bath for 10 minutes. To the resulting mixture PLURONIC® F68 (available from BASF Corporation) was added as a 100 mg/mL solution in water, reaching 5% w/w of the total coating formulation.

The topcoats were dried under hot air and left further to dry over night at room temperature. The balloons were then folded, pleated and sheathed in a nylon sheath. The balloons were subsequently placed in a 55° C. oven for 1 hour.

The full length catheters were tested according to the procedure in example 12.

Example 15:

Release of Paclitaxel from Balloons

Three full-length balloon catheters per formulation received the hydrophilic basecoat (R) according to example 1 and were top-coated with the following formulations:

Per formulation, 5-6 mg of paclitaxel was dissolved in 50 µL chloroform. The solution was dispersed in 1 mL BSA at 50 mg/mL in water using a sonic probe for 20 seconds. The obtained emulsions were spun in a centrifuge for 15 minutes at 5000 rpm. The clear supernatant was aspirated; the residue was frozen and lyophilized. The residues weighed on average 9.8 mg. To remove the remaining BSA, the solids were dispersed in 1 mL of fresh water using a sonic bath and subsequently spun for 10 minutes at 10,000 rpm. The supernatant was aspirated ("paclitaxel residue").

5 mL of a DOTAP solution at 25 mg/mL in ethanol was placed in a glass round-bottom container and evaporated under vacuum to obtain a film. The DOTAP was dispersed in 12.5 mL water by adding batches of 4.2 mL water to the glass container and briefly sonication in a sonic bath. The batches were combined, sonicated for 10 minutes in a sonic bath and filtered through a 0.45 µm filter.

Polyethyleneimine at high molecular weight 50% w/w in water (Sigma) was diluted in DDW to a 2% w/w or 20 mg/mL solution.

To the amorphous paclitaxel residues DOTAP or PEI in water was added as follows:

1. (5 µg paclitaxel) 100 µL of a DOTAP dispersion in water at 10 mg/mL was added to the paclitaxel residue. 15.8 µL was used to coat balloon material.

2. (6 µg paclitaxel) 60 µL polyethyleneimine high molecular weight (PEI-HMW) at 20 mg/mL was added with 30 µL water. 11.8 µL was used to coat balloon material.

3. (5 µg paclitaxel) 100 µL of a DOTAP dispersion in water at 10 mg/mL was added to the paclitaxel residue. Then 50 µL dextran (100 mg/mL in water) was added. The balloon was coated with 23.8 µL of this material.

4. 5 mg jar-milled paclitaxel was suspended in 75 µL water and sonicated until well dispersed. 1 mg DOTAP (40 µL DOTAP 25 mg/mL in ethanol) was added and sonicated in sonic bath for 10 minutes. 18.2 µL was used to coat balloon material.

The topcoats were dried under hot air and left further to dry over night at room temperature. The balloons were then folded, pleated and sheathed in a nylon sheath. The balloons were subsequently placed in a 55° C. oven for 1 hour.

The full length catheters were tested according to the procedure in example 12.

TABLE 3

Tissue Transfer (µg) and Standard Deviations for Examples 2-15.

| Example | Description | Active Agent Tissue transfer (µg) | Standard Deviation |
|---|---|---|---|
| Example 2 | PTX/DOTAP/siRNA | 42.05 | 15.09 |
|  | PTX/DOTAP/siRNA/glycogen | 71.29 | 13.71 |
| Example 3 | PTX + DOTAP 10% w/w | 88.44 |  |
|  | PTX + DOTAP 20% w/w | 102.68 |  |
|  | PTX + DOTAP 10% w/w + siRNA | 116.92 |  |
|  | PTX + DOTAP 20% w/w + siRNA | 107.64 |  |
|  | PTX + DOTAP 10% w/w + siRNA + F68 | 152.2 |  |
|  | PTX + DOTAP 20% w/w + siRNA + F68 | 109.8 |  |
| Example 4 | PTX(Netsch milled)/DOTAP 10:1 w/w (formulation 1) | 112.70 | 40.76 |
|  | PTX(Netsch milled)/DOTAP/F68/siRNA 10:1:0.5:0.1 w/w (formulation 2) | 112.50 | 6.70 |
|  | PTX(Jar milled)/DOTAP 10:1 w/w (formulation 3) | 82.40 |  |
|  | PTX(Jar milled)/DOTAP 5:1 w/w (formulation 4) | 154.82 | 80.47 |
|  | PTX(Jar milled)/DOTAP/F68 10:1:0.5 w/w (formulation 5) | 157.80 | 10.13 |
|  | PTX(Jar milled)/DOTAP/F68 5:1:0.5 w/w (formulation 6) | 178.94 | 0.08 |
|  | PTX(Jar milled)/DOTAP/F68/siRNA 5:1:0.5:0.1 w/w (formulation 7) | 122.64 | 8.26 |
| Example 5 | PTX/DOTAP 5:1 | 107.21 | 18.76 |
|  | PTX/DOTAP/F68 5:1:0.16 | 99.06 | 12.44 |
|  | PTX/DOTAP/Dext 5:1:5 | 116.21 | 3.34 |
| Example 6 | PTX/DOTAP 15:6 w/w | 107.8 |  |
|  | PTX/DOTAP/Gelatine B 15:3:5 w/w | 80.12 |  |
|  | PTX/DOTAP/Gelatine B 15:6:5 w/w | 78.4 |  |
|  | PTX/DOTAP/Gelatine B 15:3:15 w/w | 79.2 |  |
|  | PTX/DOTAP/Glycogen 15:3:15 w/w | 293.32 |  |
|  | PTX/DOTAP/Glycogen 15:3:5 w/w | 116.32 |  |
|  | PTX/DOTAP/Glycogen 15:6:5 w/w | 80.88 |  |
|  | PTX/DOTAP/Dextran 15:3:5 w/w | 128.76 |  |
|  | PTX/DOTAP/Dextran 15:6:5 w/w | 125.92 |  |
|  | PTX/DOTAP/Dextran 15:3:15 w/w | 172.16 |  |
| Example 7 | PTX/DOTAP/F68 5:1:0.32 w/w | 180.30 | 91.22 |
|  | PTX/DOTAP/F68 5:1:0.16 w/w | 148.46 | 41.83 |
|  | PTX/DOTAP/F68 5:1:0.04 w/w | 91.62 | 9.64 |
| Example 8 | PTX(amorphous)/DOTAP 5:1 w/w | 185.76 | 73.19 |
|  | PTX(amorphous)/PEI-LMW 5:1 w/w | 69.96 | 30.79 |
|  | PTX(amorphous)/PEI-HMW 5:1 w/w | 260.63 | 168.15 |
| Example 10 | PTX/DOTAP 5:1 | 139.8 | 6.2 |
|  | PTX/DOTAP/F68 5:1:0.32 w/w | 151.7 | 48.8 |
|  | PTX/DOTAP/F68 5:1:0.65 w/w | 80.8 | 12.6 |
|  | PTX/DOTAP/F68 5:1:1.3 w/w | 69.9 | 4.9 |
|  | PTX/DOTAP/F68 5:1:2.6 w/w | 86.7 | 17.1 |
| Example 11 | PTX only | 62.08 |  |
|  | PTX/DOTAP 5:1 w/w | 282.36 |  |
|  | PTX/chitosan 10:1 w/w | 48.32 |  |
|  | PTX/Protamine 10:1 w/w | 60.68 |  |

TABLE 3-continued

Tissue Transfer (µg) and Standard Deviations for Examples 2-15.

| Example | Description | Active Agent Tissue transfer (µg) | Standard Deviation |
|---|---|---|---|
| Example 13 | PTX/DOTAP/DEXTRAN static test | 116.94 | 5.23 |
|  | PTX/DOTAP/DEXTRAN flow test | 75.84 |  |
|  | PTX/DOTAP/gelatine A static test | 69.18 | 28.60 |
|  | PTX/DOTAP/gelatine A flow test | 7.20 |  |
|  | PTX/DOTAP/glycogen static test | 118.00 | 38.41 |
|  | PTX/DOTAP/glycogen flow test | 60.24 |  |
|  | PTX/DOTAP/Cholesterol static test | 103.98 | 3.87 |
|  | PTX/DOTAP/Cholesterol flow test | 40.64 |  |
| Example 14 | PTX/DOTAP/F68 79:16:5 w/w | 68.97 | 29.08 |
|  | PTX/DOTAP/glycogen 45.5:9:45.5 w/w | 72.57 | 19.14 |
|  | PTX/DOTAP/dextran 45.5:9:45.5 w/w | 83.28 | 38.72 |
| Example 15 | 83% PTX(amorphous)/17% DOTAP w/w | 35.89 | 7.50 |
|  | 83% PTX(amorphous)/17% PEI-HMW w/w | 65.94 | 12.57 |
|  | 45.5% PTX(amorphous)/9% DOTAP/45.5% dextran w/w | 75.67 | 14.09 |
|  | 83% PTX(jar milled)/17% DOTAP w/w | 49.12 | 13.83 |

Example 16:

PEI and PAMAM Dendrimers

Twelve balloon stubs were coated with the hydrophilic base coat (R) as described in Example 1. The following formulations were applied on top of the basecoat:

Stub #1 and #2: coating was applied from a 25% ethanol/75% methanol solution containing 75 mg/mL paclitaxel and 6.25 mg/mL polyethyleneimine (PEI-HMW) of 750 kDa. Total drug was targeted at 660 µg.

Stub #3 and #4: coating was applied from a 25% ethanol/75% methanol solution containing 75 mg/mL paclitaxel and 6.25 mg/mL polyamidoamine dendrimer (PAMAM, Gen. 4). Total drug was targeted at 660 µg.

Stub #5, #6 and #7: Paclitaxel was dissolved in chloroform at 100 mg/mL. 400 µL of this solution was emulsified in 10 mL aqueous BSA solution at 50 mg/mL using a sonic probe for 60 seconds. The resulting emulsion was lyophilized. BSA was removed from the amorphous paclitaxel by washing the solids three times with double distilled water. To 6.5 mg amorphous paclitaxel 33 µL water and 65 µL aqueous solution of PEI-HMW 20 mg/mL was added. The coating solution was vortexed and sonicated on sonic bath. Coating the tubs total drug was targeted at 660 µg.

Stub #8, #9 and #10: To a mixture of 7 mg jar-milled paclitaxel in 70 µL water was added 70 µL of an aqueous solution of PEI-HMW at 20 mg/mL. Total drug was targeted at 660 µg.

Stub #11 and #12: Mixture of jar-milled paclitaxel at 50 mg/mL in DDW with 10 mg/mL PAMAM in ethanol. PAMAM was added to the paclitaxel suspension until reaching a wt/wt ratio of 17:83 PAMAM versus paclitaxel. Total drug was targeted at 660 µg.

The topcoats were dried under hot air and left further to dry over night at room temperature. The balloons were then folded, pleated and sheathed in a nylon sheath. The balloons were subsequently placed in a 55° C. oven for 1 hour.

Release of the paclitaxel from the coating was then assessed according to the procedure as described in example 2.

Example 17:

Release of Paclitaxel from Full Length Balloon Catheters

Nine full-length balloon catheters received a hydrophilic basecoat (R) according to example 1 and were top-coated with the following formulations (n=3 per formulation):
1. 19 mg Jar-milled paclitaxel was combined with 283.6 μL distilled water and twice sonicated using a sonic probe for 20 seconds at power setting "3". 99.5 mg of the mixture was weighed out and added 62.9 μL of a solution of PEI 750 kDa 20 mg/mL in distilled water. Three catheters each were top-coated with 20.5 μL of the formulation.
2. 103.4 mg of the paclitaxel in water suspension was weighed out. 65.4 μL of a 20 mg/mL PEI 750 kDa in water solution and 65.4 μL of a 100 mg/mL dextran solution in water was added. Three catheters each were top-coated with 28 μL of the formulation.
3. Amorphous paclitaxel was obtained according to the procedure described in example 8, starting with 8 mg paclitaxel. To the paclitaxel residue 80 μL PEI of a 20 mg/mL PEI 750 kDa in water solution and 80 μL of a 100 mg/mL Dextran solution in water was added. Three catheters were top-coated with 15.8 μL of the formulation.

The topcoats were dried under hot air and left further to dry over night at room temperature. The balloons were then folded, pleated and sheathed in a nylon sheath. The balloons were subsequently placed in a 55° C. oven for 1 hour.

The full length catheters were tested according to the procedure in example 12.

Release of the paclitaxel from the coating on the stubs was assessed according to the procedure as described in example 2.

Example 18A:

Topcoat Balloon with Oleylamine

Eight balloon stubs of 15 mm length were coated with the hydrophilic base coat (R) as described in Example 1. The following formulations were applied on top of the basecoat.
1. 49.5 mg Jar-milled paclitaxel was suspended in 495 μL distilled water, vortexed and sonicated twice with sonic probe for 20 seconds. Then 495 μL PEI 750 kDa at 20 mg/mL, pH neutralized to 7 with 6N HCl, was added. Two stubs were topcoated with 10 μL of the formulation per stub.
2. Paclitaxel was dissolved in methanol at 100 mg/mL. To 50 μL of the paclitaxel solution, 50 μL of a 25 mg/mL PEI 750 kDa solution in ethanol was added. Two stubs were topcoated with 10 μL of the formulation per stub.
3. Oleylamine was dissolved in ethanol at 20 mg/mL. 25 μL was added to 75 μL of the 100 mg/mL paclitaxel solution in methanol. Two stubs were topcoated with 7 μL of the formulation per stub.

The topcoats were dried under hot air and left further to dry over night at room temperature. The balloons were then folded, pleated and sheathed in a nylon sheath. The balloons were subsequently placed in a 55° C. oven for 1 hour.

Release of the paclitaxel from the coating was then assessed according to the procedure as described in example 2.

Example 18B:

Topcoat Balloon with Polyurethanediol, Tricaprylylmethylammonium Chloride, Trimethylolpropane Ethoxylate, Pentaerythritol Ethoxylate and Jeffamine ED-900

Ten balloon stubs of 15 mm length were coated with the hydrophilic base coat (R) and top-coated as described in Example 1. The following formulations were applied on top of the basecoat. 100 mg Jar-milled paclitaxel was suspended in 1 mL distilled water and thoroughly dispersed using vortex and sonic probe.
1. Polyurethanediol 88 wt % was dissolved in water at 25 mg/mL. 55.7 mg of the paclitaxel suspension was weighed out and 40.7 μL of the polyurethanediol solution was added. Two stubs were top coated with 12.6 μL of the formulation per stub.
2. Tricaprylylmethylammonium chloride was dissolved in ethanol at 25 mg/mL. 77.4 mg of the paclitaxel suspension was weighed out and 56 μL of the Tricaprylylmethylammonium solution was added. One stub was top coated with 12.6 μL of the formulation.
3. Trimethylolpropane ethoxylate 20/3 EO/OH was dispersed in water at 25 mg/mL. 57.4 mg of the paclitaxel suspension was weighed out and 41.7 μL of the trimathylolpropane ethoxylate solution was added. Two stubs were top coated with 12.6 μL of the formulation per stub.
4. Pentaerythritol ethoxylate 15/4 EO/OH was dissolved in water at 25 mg/mL. 67.9 mg of the paclitaxel suspension was weighed out and 49.4 μL of the Pentaerythritol ethoxylate solution was added. Two stubs were topcoated with 12.6 μL of the formulation per stub.
5. Jeffamine ED-900 was dissolved in water at 25 mg/mL. 59.8 mg of the paclitaxel suspension was weighed out and 43.5 μL of the Jeffamine solution was added. Two stubs were top coated with 12.6 μL of the formulation per stub.

The balloons were folded, pleated and sheathed in a nylon sheath. The balloons were subsequently placed in a 55° C. oven for 1 hour.

Release of the paclitaxel from the coating was then assessed according to the procedure as described in example 2.

Example 19:

Synthesized Linear and Branched PEI

The following compounds were synthesized based on dodecane-epoxylation of spermine, triethylamine glycol, 1-methyl-propyldiamine or other amine derivatives

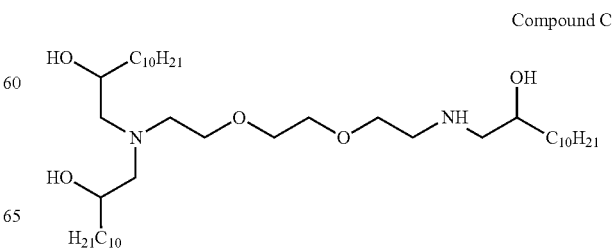

Compound C

Compound D

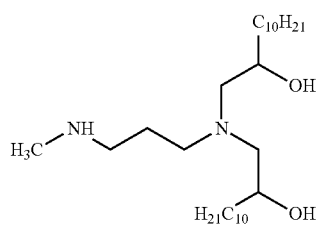

Compound E

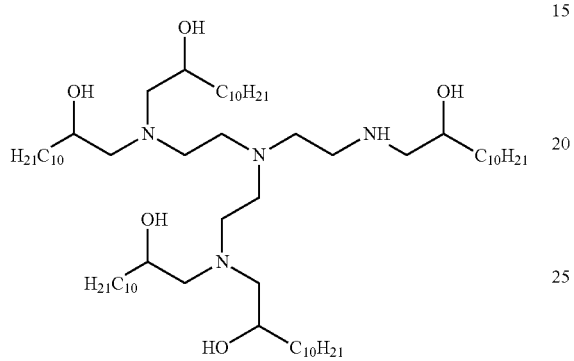

Compound F

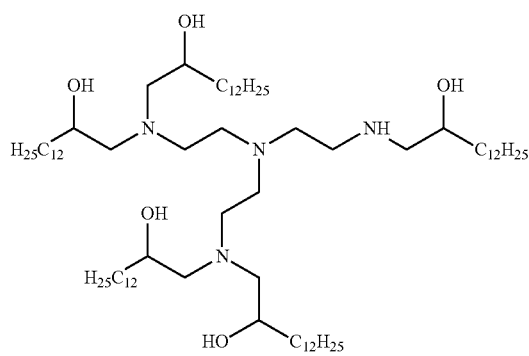

Compound G

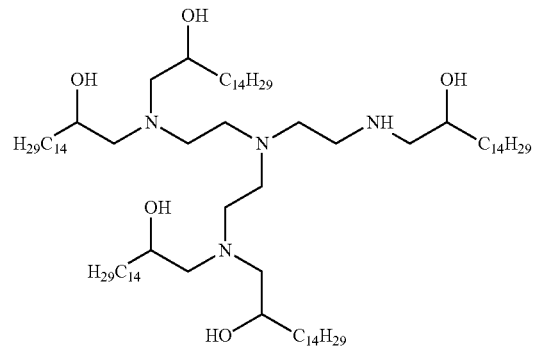

Compound H

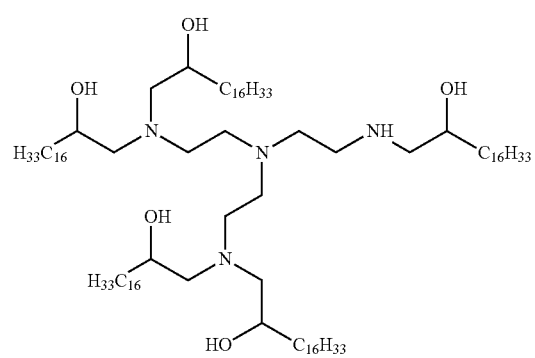

Balloon stubs (22) were coated with the hydrophilic base coat (R) and received a topcoat as described in Example 1.

Preparation of formulations for the topcoats: Jar-milled paclitaxel was suspended in water at 100 mg/mL and thoroughly dispersed using vortex and two times probe-sonication for 20 seconds at setting "2.5". All of the following formulations were prepared by weighing out paclitaxel suspension and adding a solution of an additive such that the w/w ratio of paclitaxel versus additive was 83:17% w/w. The resulting mixtures were vortexed thoroughly and placed in a sonic bath for 10 minutes prior to applying the coating. Formulations (12.6 μL) were applied on top of the basecoat of each of 2 stubs and one metal coupon per formulation. The procedures for coating the stubs as described in example 1 were followed. The coatings on the metal coupons were weighed after the coating was completely dry.

TABLE 4

Variable Values for Example 19.

| Nr. | Paclitaxel suspension (mg) | Additive | Conc. (mg/mL) | Solvent of additive | Amount (μL) | Added water (μL) | Coating weight (μg) |
|---|---|---|---|---|---|---|---|
| 1 | 41 | Trolamine | 20 | water | 37.3 | N/A | 683 |
| 2 | 45.7 | Compound C | 25 | ethanol | 33.2 | 83 | 777 |
| 3 | 41.1 | Compound D | 25 | ethanol | 29.9 | 7.5 | 647 |
| 4 | 40.3 | Compound E | 25 | ethanol | 29.3 | 7.3 | 778 |
| 5 | 41.1 | Linear PEI 2.5 kDa | 20 | warm water | 37.4 | N/A | 692 |
| 6 | 38.7 | Linear PEI 25 kDa | 20 | warm water | 35.2 | N/A | 656 |
| 7 | 45.3 | Linear PEI 250 kDa | 20 | warm water | 41.2 | N/A | 717 |
| 8 | 38.9 | Branched PEI 1.2 kDa | 20 | water | 35.4 | N/A | 822 |
| 9 | 44.7 | Branched PEI 10 kDa | 20 | water | 40.6 | N/A | 774 |

TABLE 4-continued

| | | Variable Values for Example 19. | | | | | |
|---|---|---|---|---|---|---|---|
| Nr. | Paclitaxel suspension (mg) | Additive | Conc. (mg/mL) | Solvent of additive | Amount (μL) | Added water (μL) | Coating weight (μg) |
| 10 | 52.0 | Branched PEI 50-100 kDa | 20 | water | 47.3 | N/A | 795 |

Numbers 5-10 in Table 4 (PEI polymers) were purchased from Polysciences, Inc.

The coated balloon stubs were dried under hot air and left further to dry over night at room temperature. The balloons were folded, pleated and sheathed in a nylon sheath. The balloons were subsequently placed in a 55° C. oven for 1 hour.

Release of the paclitaxel from the coating was then assessed according to the following procedure. Excised pig coronary arteries (Pel-Freez Biologicals) were prepared, placed in a plastic tube and kept at 37° C. Upon removal of the sheaths from the balloon stubs, the stubs were fixed to a motor and turned at a speed 125 rpm and immersed in Fetal Bovine Serum (FBS) at 37° C. for 30 seconds. The balloons were removed from the FBS (methanol was then added to the FBS at a 1:3 FBS/methanol ratio by volume in order to dissolve the paclitaxel). Next, the balloon was expanded in the artery tissue at 60-80 psi for 30 seconds while immersed in regular PBS at 37° C. and after deflation and removal of the balloon, the artery tissue was removed from the plastic tube and rinsed with PBS at 37° C. After removal of the balloon from the tissue and rinsing of the tissue, was placed in a methanol/0.1% acetic acid solution. The resulting methanol and acetic acid solution was tested for paclitaxel content using HPLC ("Drug Transfer to Tissue"). The balloon was also placed in methanol and 0.1% acetic acid solution.

Example 20:

Crystalline (Jar Milled vs Sonicated) vs Amorphous Paclitaxel

Balloon stubs (22) were coated with the hydrophilic base coat (R) and received a paclitaxel containing topcoat as described in Example 1. The following formulations were coated on balloon-stubs with hydrophilic base-coat R (n=2 per formulation).

a) Paclitaxel (75 mg) was dissolved in 750 μL methanol. Paclitaxel solution (75 μL) was mixed with 25 μL of a PEI 750 kDa solution at 25 mg/mL in ethanol. 8.8 μL of the resulting solution was applied as top-coat on two stubs.

b) Jar-milled paclitaxel was suspended in water at 100 mg/mL and thoroughly dispersed using vortex and two times probe-sonication for 20 seconds at setting "2.5". All of the following formulations were prepared by weighing out paclitaxel suspension and adding a solution of an additive such that the w/w ratio of paclitaxel versus additive was 83:17% w/w. The resulting mixtures were vortexed thoroughly and placed in a sonic bath for 10 minutes prior to applying the coating. 13.9 μL of the resulting solution was applied as top-coat on two stubs.

TABLE 5

| | | Variable Values for Example 20. | | | | |
|---|---|---|---|---|---|---|
| Nr. | Paclitaxel suspension (mg) | Additive | Conc. (mg/mL) | Solvent of additive | Amount (μL) | Added water (μL) |
| | 84.8 | PEI 750 kDa | 20 | Water (add HCl to pH 7.0) | 77.0 | N/A |
| | 90.6 | Tricaprylyl methylamine | 25 | ethanol | 65.8 | 16.5 |
| | 91.5 | Spermine | 20 | water | 83.2 | N/A |
| | 90.4 | Compound A | 25 | ethanol | 65.7 | 16.5 |
| | 95.3 | Compound B | 25 | ethanol | 69.3 | 17.3 |
| | 90.3 | Compound F | 25 | ethanol | 65.7 | 16.4 |
| | 96.7 | Compound G | 25 | ethanol | 70.3 | 17.6 |
| | 86.5 | Compound H | 25 | ethanol | 62.9 | 15.7 |
| | 91.8 | L-ornithine | 20 | water | 83.4 | N/A |
| | 88.9 | Choline•HCl | 20 | water | 80.8 | N/A |

The coated balloon stubs were dried under hot air and left further to dry over night at room temperature. The balloons were folded, pleated and sheathed in a nylon sheath. The balloons were subsequently placed in a 55° C. oven for 1 hour.

Release of the paclitaxel from the coating was then assessed according to the following procedure. Excised pig coronary arteries (available from Pel-Freez Biologicals) were prepared, placed in a plastic tube and kept at 37° C. Upon removal of the sheaths from the balloon stubs, the stubs were fixed to a motor and turned at a speed 125 rpm and immersed in Horse Serum (HS) at 37° C. for 30 seconds. The balloons were removed from the HS. Next, the balloon was expanded in the artery tissue at 60-80 psi for 30 seconds while immersed in regular PBS at 37° C. and after deflation and removal of the balloon, the artery tissue was removed from the plastic tube and rinsed with PBS at 37° C. After removal of the balloon from the tissue and rinsing of the tissue, was placed in a methanol/0.1% acetic acid solution. The resulting methanol and acetic acid solution was tested for paclitaxel content using HPLC ("Drug Transfer to Tissue"). The balloon was also placed in methanol and 0.1% acetic acid solution.

Example 21:

PEI, L-Citruline, Poly-L-Ornithine and Poly-L-Glutamic Acid

Nine balloon stubs were coated with the hydrophilic base coat (R) and received a top-coat as described in Example 1.

Preparations for the topcoats: Jar-milled paclitaxel was suspended in water at 100 mg/mL and thoroughly dispersed using vortex and two times probe-sonication for 20 seconds at setting "2.5". All of the following formulations were prepared by weighing out 50 mg of the paclitaxel suspension and adding 45.5 μL of a 20 mg/mL of an aqueous solution of the additives such that the w/w ratio of paclitaxel versus additives was 83:17% w/w. The resulting mixtures were vortexed thoroughly and placed in a sonic bath for 10 minutes prior to applying the coating. The following additives were used:

(1) PEI 750 kDa; added HCl to pH 7.0
(2) L-citruline
(3) poly-L-ornithine
(4) poly-L-glutamic acid The resulting formulation (13.9 μL) was applied as a topcoat on stubs (n=3 for PEI, n=2 per formulation for other additives).

The coated stubs were dried under hot air and left further to dry over night at room temperature. The balloons were folded, pleated and sheathed in a nylon sheath. The balloons were subsequently placed in a 55° C. oven for 1 hour.

Release of the paclitaxel from the coating was assessed according to the procedure described in example 20.

Example 22:

Branched PEI with Oleic Acid Grafts and Amino Acid Methyl Esters

Eight balloon stubs were coated with the hydrophilic base coat (R) and received a top-coat as described in Example 1. Jar-milled paclitaxel was suspended in water at 100 mg/mL and thoroughly dispersed using vortex and two times probe-sonication for 20 seconds at setting "2.5". All of the following formulations were prepared by weighing out paclitaxel suspension and adding a solution of an additive such that the w/w ratio of paclitaxel versus additive was 83:17% w/w.

TABLE 6

Variable Values for Example 22.

| Nr. | Paclitaxel suspension (mg) | Additive | Conc. (mg/mL) | Solvent of additive | Amount (μL) |
|---|---|---|---|---|---|
| 1 | 92.7 | spermine-oleate (ethanol) | 20 | ethanol | 84.3 |
| 2 | 90.7 | PEI(10 kDa)-oleate 2:1 (ethanol | 20 | ethanol | 82.4 |
| 3 | 89.0 | PEI 750 kDa-oleate 1:1 (ethanol) | 20 | water | 80.9 |
| 4 | 95.4 | PEI(1200 Da)-oleate 2:1 (water) | 20 | ethanol | 86.7 |

The resulting mixtures were vortexed thoroughly and placed in a sonic bath for 10 minutes prior to applying the coating. The resulting solution (13.8 μL) was applied as top-coat on each of two stubs. The coated stubs were dried under hot air and left further to dry over night at room temperature. The balloons were folded, pleated and sheathed in a nylon sheath. The balloons were subsequently placed in a 55° C. oven for 1 hour.

Release of the paclitaxel from the coating was assessed according to the procedure described in example 20.

Example 23:

PAMAM Derivatives

In this study various different PAMAMs were investigated with either acid (COOH) end groups or similar generation-4 amine end groups with different building blocks.

The chemical formula of PAMAM $4^{th}$ gen—polyamidoamine dendrimer, based on an ethylenediamine core is as follows:

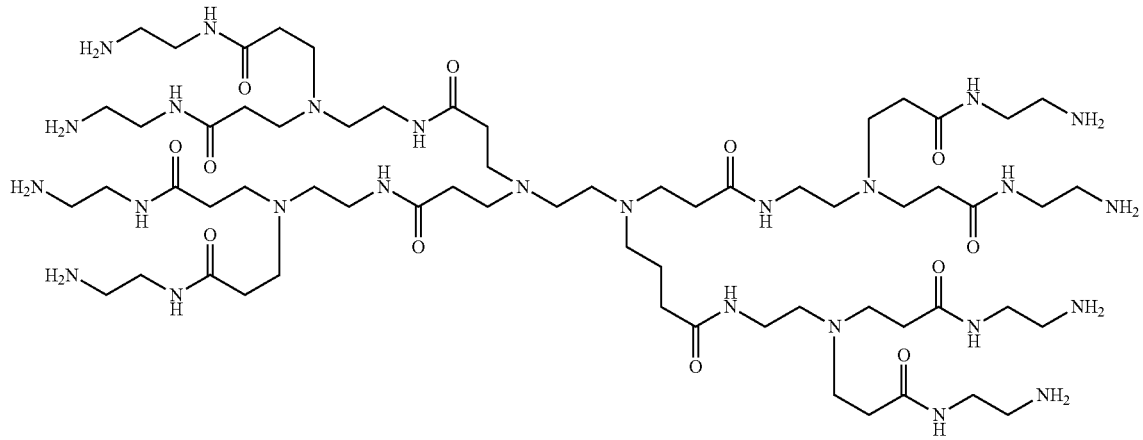 [SMILES: NCCNC(=O)CCN(CCNC(=O)CCCN(CCC(=O)NCCN(CCC(=O)NCCN)CCC(=O)NCCN)CCN(CCC(=O)NCCN(CCC(=O)NCCN)CCC(=O)NCCN)CCC(=O)NCCN(CCC(=O)NCCN)CCC(=O)NCCN)CCC(=O)NCCN]

Fifteen balloon stubs were coated with the hydrophilic base coat (R) as described in Example 1.

Preparations for the Topcoats:

Approximately 10 mg sonicated paclitaxel (see experiment 1) was weighed out and suspended in water at 100 mg/mL. A solution of a PAMAM was added to the paclitaxel suspension such that the w/w ratio of paclitaxel versus additives was 83:17% w/w. The resulting mixtures were vortexed thoroughly and two times probe-sonication for 20 seconds at setting "2.5" and placed in a sonic bath for 10 minutes prior to use for applying the top-coat (applied according to procedure in Example 1). Three stubs were coated per formulation.

TABLE 7

Variable Values for Example 23

| Num. | PAMAM | CAS No. | Conc. (mg/mL) | Solvent of additive | Amount (μL) | Added methanol (μL) |
|---|---|---|---|---|---|---|
| 1 | Gen 4 | 163442-67-9 | 100 | methanol | 20 | N/A |
| 2 | Gen 1.5 | 202009-64-1 | 200 | methanol | 10 | 10 |
| 3 | Gen 3.5 | 192948-77-9 | 100 | methanol | 20 | N/A |
| 4 | Gen 4 (Dab-Am-4) | 120239-63-6 | 100 | methanol | 10 | N/A |
| 5 | Gen 4 (hexyl) | Not assigned; Sigma Cat. No.: 640921 | 100 | methanol | 10 | N/A |

The topcoats were dried under hot air and left further to dry over night at room temperature. The balloons were folded, pleated and sheathed in a nylon sheath. The balloons were subsequently placed in a 55° C. oven for 1 hour.

Release of the paclitaxel from the coating was assessed according to the procedure described in example 20.

Example 24:

PAMAM with Different Molecular Weights

PAMAM is a polyamidoamine dendrimer (i.e. contains both amide and amine groups; see exemplary chemical structure below).

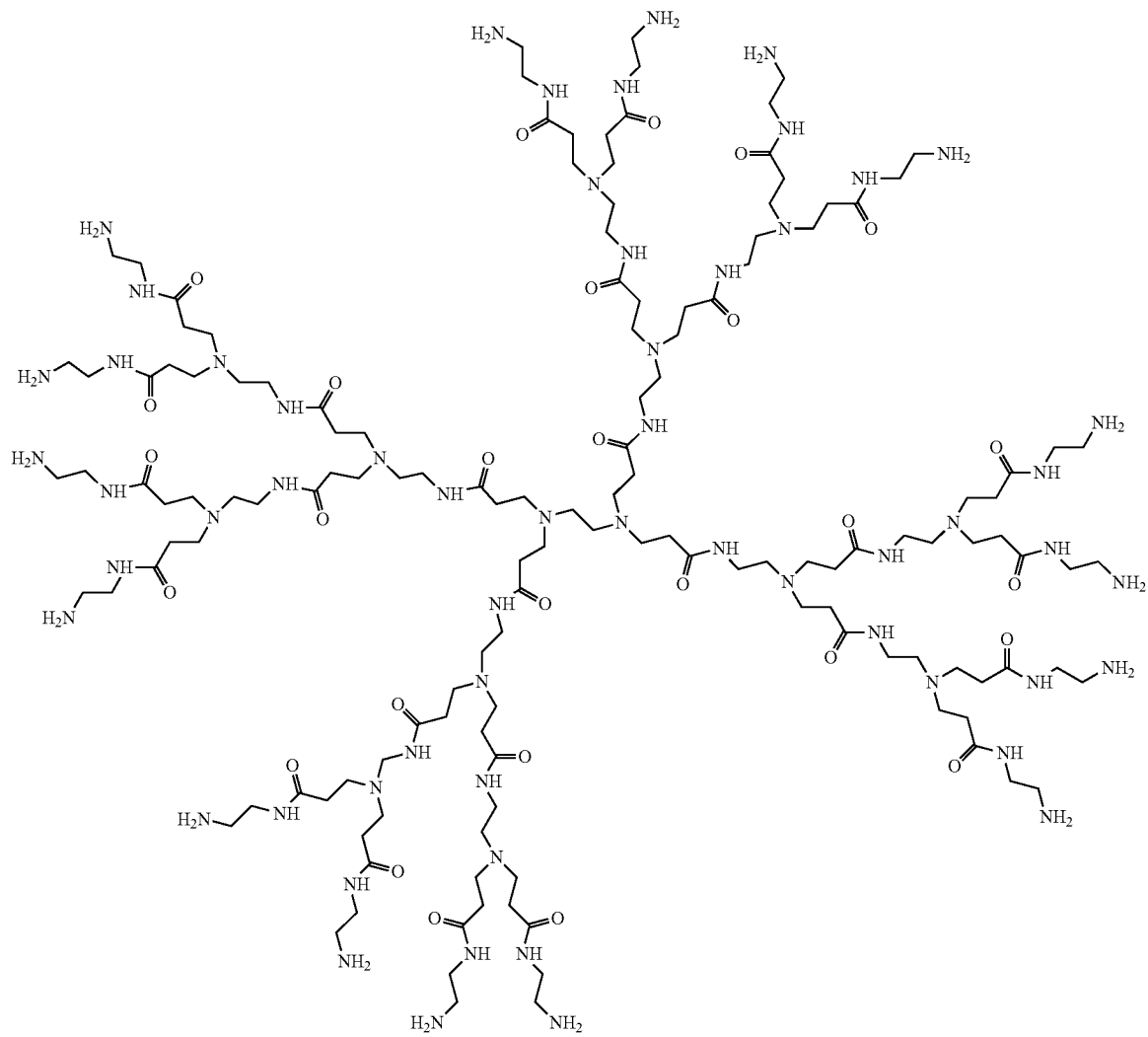 [SMILES: NCCNC(=O)CCN(CCNC(=O)CCN(CCNC(=O)CCN(CCC(=O)NCCN(CCC(=O)NCCN(CCC(=O)NCCN)CCC(=O)NCCN)CCC(=O)NCCN(CCC(=O)NCCN)CCC(=O)NCCN)CCN(CCC(=O)NCCN(CCC(=O)NCCN(CCC(=O)NCCN)CCC(=O)NCCN)CCC(=O)NCCN(CCC(=O)NCCN)CCC(=O)NCCN)CCC(=O)NCCN(CCC(=O)NCCN(CCC(=O)NCCN)CCC(=O)NCCN)CCC(=O)NCN(CCC(=O)NCCN)CCC(=O)NCCN)CCC(=O)NCCN(CCC(=O)NCCN)CCC(=O)NCCN)CCC(=O)NCCN]

PAMAM is a globulin polymer and synthesized in generations: every following generation, as the molecular weight increased it is accompanied by an exponential increase in number of branches. In this example a series of generations was tested at both 90:10 and 75:25 PTX/PAMAM.

Twenty eight balloon stubs were coated with the hydrophilic base coat (R) and received a top-coat as described in Example 1.

Preparations for the Topcoats:

PAMAM solutions of generation 0, 1, 2, 3, 4, 5, and 7 with ethylene diamine core were obtained (available from Sigma) and diluted in methanol to 50 mg/mL. Sonicated paclitaxel (see experiment 1) was suspended in water at 50 mg/mL and thoroughly dispersed using vortex and two times probe-sonication for 20 seconds at setting "2.5".

TABLE 8

CAS Nos. for PAMAM Derivatives.

| PAMAM Gen | CAS No. |
| --- | --- |
| 0 | 155773-72-1 |
| 1 | 142986-44-5 |
| 2 | 93376-66-0 |
| 3 | 153891-46-4 |
| 4 | 163442-67-9 |
| 5 | 163442-68-0 |
| 7 | 163442-70-4 |

A. Paclitaxel/PAMAM formulations at 90:10 w/w ratio.
  Paclitaxel (50 mg) suspension was weighed out and 5.3 µL of a PAMAM solution at 50 mg/mL in methanol was added. The formulations were placed in a sonic bath for 10 minutes before it was used to apply the top-coat. Two stubs were coated per formulation.

B. Paclitaxel/PAMAM formulations at 75:25 w/w ratio.
  Paclitaxel suspension (50 mg) was weighed out and 15.9 µL of a PAMAM solution at 50 mg/mL in methanol was added. The formulations were placed in a sonic bath for 10 minutes before it was used to apply the top-coat. Two stubs each were coated per formulation.

The topcoats were dried under hot air and left further to dry over night at room temperature. The balloons were folded, pleated and sheathed in a nylon sheath. The balloons were subsequently placed in a 55° C. oven for 1 hour. Release of the paclitaxel from the coating was assessed according to the procedure described in example 20.

TABLE 9

Tissue Transfer (µg) and Standard Deviations for Examples 16-24.

| Example | Description | Active Agent Tissue transfer (µg) | Standard Deviation |
| --- | --- | --- | --- |
| Example 16 | PEI-HMW/PTX 8:92 w/w in methanol (1, 2) | 254.68 | 34.51 |
| | PAMAM/PTX 8:92 w/w in methanol (3, 4) | 259.80 | 35.47 |
| | PEI-HMW/PTX(amorphous) 17:83 w/w (5, 6, 7) | 14.25 | 3.81 |
| | PEI-HMW/PTX(jar milled) 17:83 w/w (8, 9, 10) | 149.36 | 19.94 |
| | PAMAM/PTX(jar milled) 17:83 w/w (11, 12) | 189.46 | 0.76 |
| Example 17 | 83% PTX(jar milled)/ 17% PEI-HMw w/w | 120.98 | 14.86 |
| | 45.5% PTX(jar milled)/ 9% PEI-HMw/ 45.5% dextran w/w | 27.53 | 1.84 |
| | 45.5% PTX(amorphous)/ 9% PEI-HMw/ 45.5% dextran | 115.83 | 34.10 |
| Example 18A | PEI/PTX 20:80 w/w in methanol | 240.53 | 71.69 |
| | Oleylamine/PTX 8:92 w/w in methanol | 96.60 | 33.94 |
| | PEI/PTX(sonicated) 17:83 w/w pH 7.0 | 76.66 | 17.68 |
| Example 18B | Polyurethanediol | 42.84 | 21.72 |
| | Tricaprylylmethylammonium Chloride | 327.84 | |
| | Trimethylolpropane ethoxylate | 88.42 | 40.25 |
| | Pentaerythritol ethoxylate | 20.06 | 7.27 |
| | Jeffamine ED-900 | 37.52 | 5.88 |
| Example 19 | Trolamine | 21.58 | 5.52 |
| | Compound C | 127.06 | 13.55 |
| | Compound D | 96.74 | 25.54 |
| | Compound E | 59.72 | 15.27 |
| | Linear PEI 2.5 kDa | 96.46 | 74.25 |
| | Linear PEI 25 kDa | 43.88 | 14.20 |
| | Linear PEI 250 kDa | 42.66 | 4.95 |
| | Branched PEI 1.2 kDa | 55.00 | 13.97 |
| | Branched PEI 10 kDa | 127.70 | 37.87 |
| | Branched PEI 50-100 kDa | 177.82 | 41.95 |
| Example 20 | PTX/PEI 750 kDa 92:8 w/w in methanol | 27.90 | 2.86 |
| | PTX/PEI 750 kDa 83:17 w/w jar milled | 145.44 | 1.53 |
| | Tricaprylyl methylamine | 123.32 | 56.57 |
| | Spermine | 38.10 | 9.87 |
| | Compound A | 84.64 | 10.86 |
| | Compound B | 47.94 | 11.34 |
| | Compound F | 44.28 | 8.09 |
| | Compound G | 25.60 | 23.14 |
| | Compound H | 32.66 | 2.57 |
| | L-ornithine | 52.82 | 1.10 |
| | Choline•HCl | 36.28 | 11.99 |
| Example 21 | PEI 750 kDa, pH 7.0 | 179.8 | 62.83 |
| | L-citruline | 56.62 | 9.02 |
| | poly-L-ornithine | 113.4 | 21.10 |
| | poly-L-glutamic acid | 34.3 | 6.76 |
| Example 22 | spermine-oleate (ethanol) | 84.08 | 10.74802 |
| | PEI(10 kDa)-oleate 2:1 (ethanol) | 41.94 | 1.612203 |
| | PEI 750 kDa-oleate 1:1 (ethanol) | 28.62 | 12.13395 |
| | PEI(1200 Da)-oleate 2:1 (water) | 63.28 | 9.842926 |
| Example 23 | PAMAM Gen 4 (163442-67-9) | 100.89 | 35.93021 |
| | PAMAM Gen 1.5 (202009-64-1) | 31.68 | 11.23829 |
| | PAMAM Gen 3.5 (192948-77-9) | 43.24 | 3.178931 |
| | PAMAM Gen 4 (Dab-Am-4; (120239-63-6) | 15.88 | 8.566633 |
| | PAMAM Gen 4 (hexyl; Sigma cat. No.: 640921) | 30.68 | 20.23051 |
| Example 24 | 10:90 PAMAM:PTX; w/w | | |
| | PAMAM gen 0 | 47.32 | 18.83732 |
| | PAMAM gen 1 | 57.6 | 16.06547 |
| | PAMAM gen 2 | 103.22 | 47.60243 |
| | PAMAM gen 3 | 82.56 | |
| | PAMAM gen 4 | 176.26 | 10.15405 |
| | PAMAM gen 5 | 129.24 | 42.36984 |
| | PAMAM gen 7 | 123.72 | 17.02713 |
| | 25:75 PAMAM:PTX w/w | | |
| | PAMAM gen 0 | 41.54 | 2.008183 |
| | PAMAM gen 1 | 26.7 | 3.196123 |
| | PAMAM gen 2 | 58.72 | 4.186072 |
| | PAMAM gen 3 | 124.88 | |
| | PAMAM gen 4 | 107.86 | 5.854844 |
| | PAMAM gen 5 | 92.78 | 8.513566 |
| | PAMAM gen 7 | 105.92 | 49.78032 |

Example 25:

Microparticles with Modified Zeta-Potential

Microparticles with rapamycin were prepared by dissolving rapamycin (100 mg; available from L C Laboratories, Woburn, Mass.) and SYNBIOSYS™ polymer (200 mg; GAPEGCL-GALA; available from InnoCore Pharmaceuticals, Groningen, Netherlands) in ethylacetate. The aqueous continuous phase (1% or 0.1% polyacrylic acid; available from Sigma Chemicals; in water at pH 7) was saturated with ethylacetate. 3 mL of the rapamycin-SYNBIOSYS™ polymer-ethylacetate solution was homogenized (at 5000 rpm for 1 minute) into 100 mL of one of the continuous phases. The ensuing mixture was poured into 500 mL deionized water and microparticles were isolated by centrifugation and washed 3x with deionized water.

Figure 10:
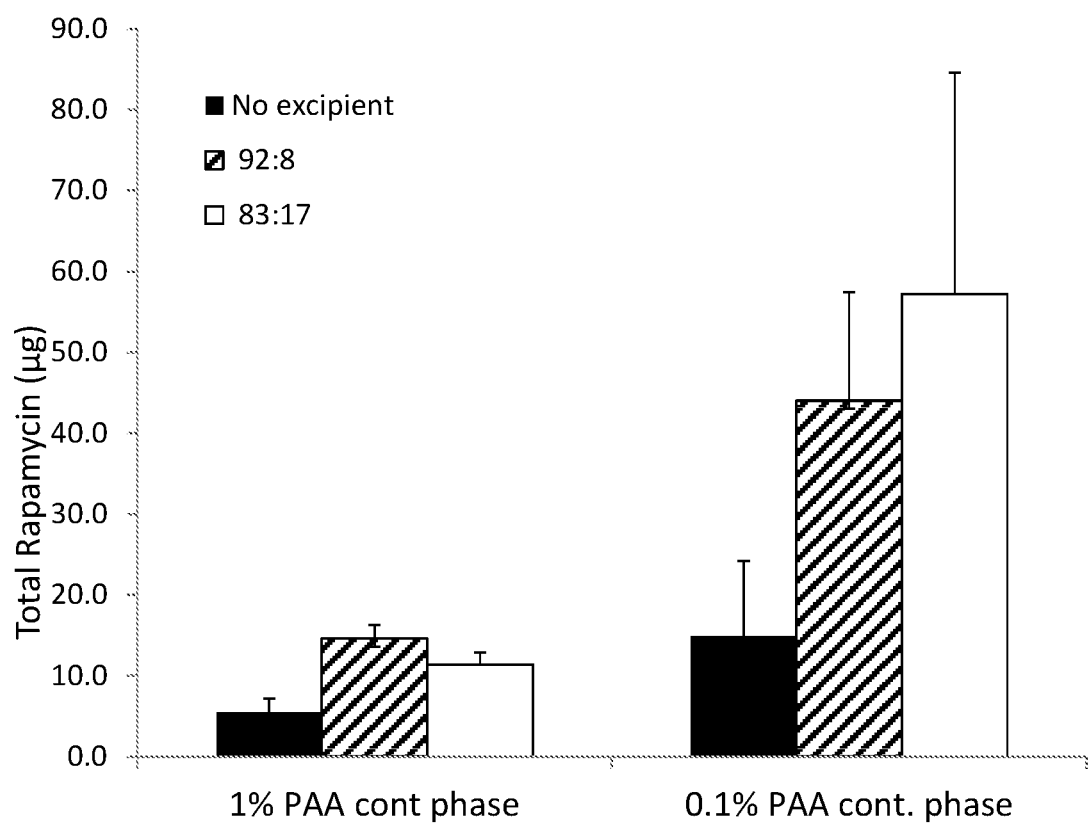
FIG. 10 is a graph of the adhesion of microparticles to MATRIGEL® plates with no excipient and using polyethyleneimine (PEI) as an excipient, and polyacrylic acid (PAA).

MATRIGEL® coated 96-well plates (Corning) were conditioned with 100 ECM cell medium for 1 hour at 37° C. Suspensions were prepared of 11 mg/mL microspheres in an aqueous solution of PEI 70 kDa (Polysciences) at 1 mg/ml or 2 mg/mL, the pH of the solutions was adjusted to pH 7 with HCl. 5 µL of the formulations was pipetted in the 100 µL medium in wells of the MATRIGEL® coated well-plate and left for 3 minutes. All wells were then rinsed 3 times with 200 µL PBS. Rapamycin adsorbed to the 96-well surface was dissolved in acetonitrile/0.1% AcOH and quantified by HPLC. FIG. 10 shows the adhesion of microparticles to MATRIGEL® plates with no excipient and using PEI as an excipient at 92:8 or 83:17 w/w particle/excipient ratios, and polyacrylic acid (PAA) at 1.0% w/w and 0.1% w/w in the continuous phase.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference. To the extent inconsistencies arise between publications and patent applications incorporated by reference and the present disclosure, information in the present disclosure will govern.

The invention has been described with reference to various specific and preferred embodiments and techniques. However, it should be understood that many variations and modifications may be made while remaining within the spirit and scope of the invention.

The invention claimed is:

1. A medical device comprising
   a catheter shaft;
   a balloon disposed around the catheter shaft, the balloon comprising an underlying polymeric layer, the polymeric layer comprising an outer surface;
   a positively charged hydrophilic polymeric layer disposed on the outer surface of the underlying polymeric layer;
   a matrix disposed on the positively charged hydrophilic polymeric layer, the matrix comprising
   a particulate hydrophobic therapeutic agent; and
   a cationic agent selected from the group consisting of cationic lipids, neutral lipids with cationic groups, and cationic polymers;
   wherein the particulate hydrophobic agent coexists in the matrix with the cationic agent.

2. The medical device of claim 1, the particulate hydrophobic therapeutic agent having an average diameter of between 100 nm and 10 µm.

3. The medical device of claim 1, the cationic agent having a molecular weight of between 2.5 kDa and 2,000 kDa.

4. The medical device of claim 1, the cationic agent having a molecular weight of between 50 kDa and 100 kDa.

5. The medical device of claim 1, the particulate hydrophobic therapeutic agent and the cationic agent forming coated therapeutic agent particles.

6. The medical device of claim 1, the cationic agent selected from the group consisting of polyethyleneimine and DOTAP.

7. A device for delivering a therapeutic agent to a vessel wall comprising:
   a polymeric balloon disposed on a catheter, the polymeric balloon comprising an underlying polymeric layer comprising an outer surface;
   a positively charged hydrophilic polymeric layer disposed on the outer surface of the underlying polymeric layer; and
   a therapeutic agent composition disposed on the positively charged hydrophilic polymeric layer, the therapeutic agent composition consisting essentially of an antiproliferative agent and a cationic polymer, wherein the cationic polymer is selected from the group consisting of a polyamine, a polyimine, a cationic polypeptide, or combinations thereof.

8. The device of claim 7, the antiproliferative agent selected from paclitaxel and sirolimus (rapamycin).

9. The device of claim 7, the cationic polymer comprising polyethyleneimine.

10. The device of claim 7, the polypeptide comprising at least one of poly-L-lysine, poly-L-ornithine, and poly(4-hydroxy-L-proline ester).

11. The device of claim 7, wherein the percent ratio of cationic polymer to antiproliferative agent is from about 97/3 to about 88/12 wt./wt.

12. The device of claim 7, wherein inflation of the polymeric balloon after insertion of the device into a vessel causes the therapeutic agent composition to contact a wall of the vessel and be transferred thereto.

13. The device of claim 12, wherein contact with the wall of the vessel causes at least some of the therapeutic agent to be transferred to the wall of the vessel within 30 seconds.

14. A method of forming a device for delivering a therapeutic agent to a vessel wall comprising:
   providing a polymeric balloon disposed on a catheter, the polymeric balloon comprising an underlying polymeric layer comprising an outer surface;

disposing a positively charged hydrophilic polymeric layer disposed onto the outer surface of the underlying polymeric layer; and disposing a therapeutic agent composition onto the positively charged hydrophilic polymeric layer; the therapeutic agent composition consisting essentially of an antiproliferative agent and a cationic polymer, wherein the cationic polymer is selected from the group consisting of a polyamine, a polyimine, a cationic polypeptide, or combinations thereof.

15. The method of claim 14, the antiproliferative agent selected from paclitaxel and sirolimus (rapamycin).

16. The method of claim 14, the cationic polymer comprising polyethyleneimine.

17. The method of claim 14, the polypeptide comprising at least one of poly-L-lysine, poly-L-ornithine, and poly(4-hydroxy-L-proline ester).

18. The method of claim 14, wherein the percent ratio of cationic polymer to antiproliferative agent is from about 97/3 to about 88/12 wt./wt.

19. The method of claim 14, wherein inflation of the polymeric balloon after insertion of the device into a vessel causes the therapeutic agent composition to contact a wall of the vessel and be transferred thereto.

20. The method of claim 14, wherein contact with the wall of the vessel causes at least some of the therapeutic agent to be transferred to the wall of the vessel within 30 seconds.

\* \* \* \* \*